(12) United States Patent
Bearup et al.

(10) Patent No.: US 7,717,457 B2
(45) Date of Patent: May 18, 2010

(54) STROLLER WITH SPRING-ASSISTED FOLD MECHANISM

(75) Inventors: Adam D. Bearup, Shillington, PA (US); Curtis M. Hartenstine, Birdsboro, PA (US); Zhong Zhi-Ren, Taipei (TW); Cui Zong-Wang, Taipei (TW)

(73) Assignee: Wonderland Nurserygoods Co., Ltd. (TW)

( * ) Notice: Subject to any disclaimer, the term of this patent is extended or adjusted under 35 U.S.C. 154(b) by 11 days.

(21) Appl. No.: 11/747,815

(22) Filed: May 11, 2007

(65) Prior Publication Data

US 2007/0262565 A1 Nov. 15, 2007

Related U.S. Application Data

(60) Provisional application No. 60/800,572, filed on May 15, 2006, provisional application No. 60/833,433, filed on Jul. 26, 2006, provisional application No. 60/868,937, filed on Dec. 7, 2006, provisional application No. 60/887,611, filed on Feb. 1, 2007.

(51) Int. Cl.
*B62B 7/00* (2006.01)

(52) U.S. Cl. ................ 280/647; 280/642; 280/650; 280/657; 280/658

(58) Field of Classification Search .......... 280/642, 280/647, 650, 657, 658
See application file for complete search history.

(56) References Cited

U.S. PATENT DOCUMENTS 2,395,208 A * 2/1946 Wylie ................. 280/642
2,751,232 A * 6/1956 Sundberg ............ 280/644
3,873,116 A    3/1975 Perego ............... 280/36 B
4,077,641 A * 3/1978 Perego ............... 280/42
4,335,893 A * 6/1982 Carmichael et al. .. 280/42
4,529,219 A * 7/1985 Shamie ............... 280/642
4,605,243 A * 8/1986 Glaser ................ 280/642
4,632,420 A * 12/1986 Miyagi ............... 280/642
5,106,116 A * 4/1992 Chen .................. 280/642
5,871,227 A * 2/1999 Huang ................ 280/642
6,357,784 B1 * 3/2002 Mitzman ............. 280/642
6,478,328 B1 * 11/2002 Yeh et al. ............ 280/650
6,715,783 B1    4/2004 Hanson ............... 280/642
6,860,504 B2 * 3/2005 Suga et al. .......... 280/642

* cited by examiner

*Primary Examiner*—Lesley Morris
*Assistant Examiner*—Katy Meyer
(74) *Attorney, Agent, or Firm*—Miller Law Group, PLLC

(57) ABSTRACT

A spring-assisted fold mechanism for a child's stroller is operable to collapse the stroller frame into a storage configuration upon actuation of a release mechanism controlling the stroller fold latch mechanism. The stroller includes a spring device interconnecting two of the pivotally connected frame components to urge the pivotal movement thereof into a collapsed, folded configuration. An anti-fold latch mechanism is associated with the stroller seat to move from an inoperative position into a locking position whenever a child is placed into the stroller seat to prevent the fold mechanism from collapsing the frame of the stroller until the child is removed from the seat. The spring device can be configured as a gas spring, a torsion spring, a compression spring or an elastomeric member that can be stretched to exert a biasing force on the stroller frame to urge movement into the collapsed position.

28 Claims, 19 Drawing Sheets

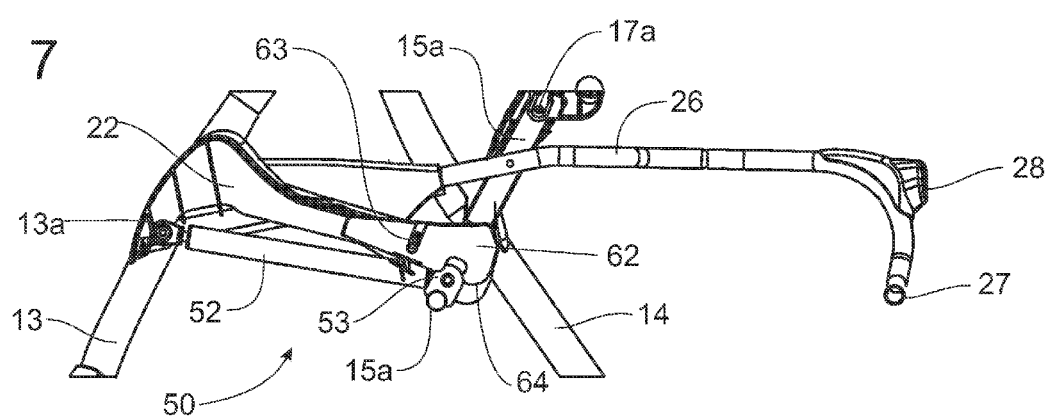
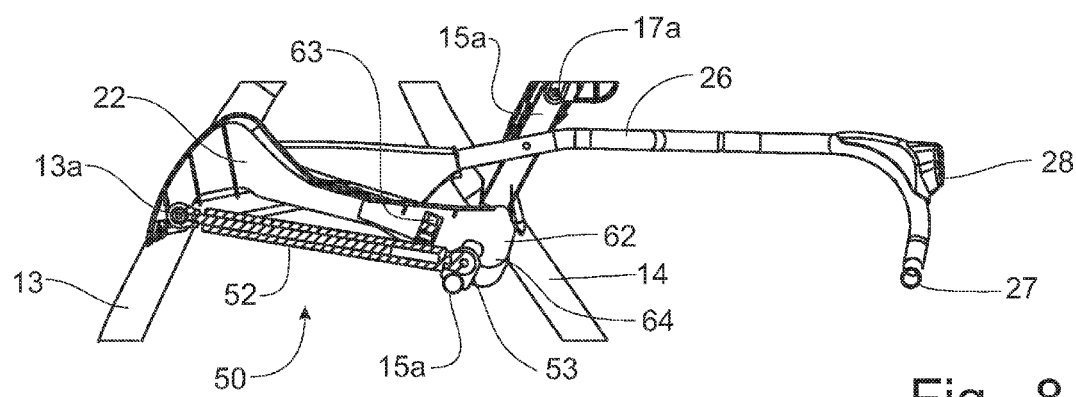

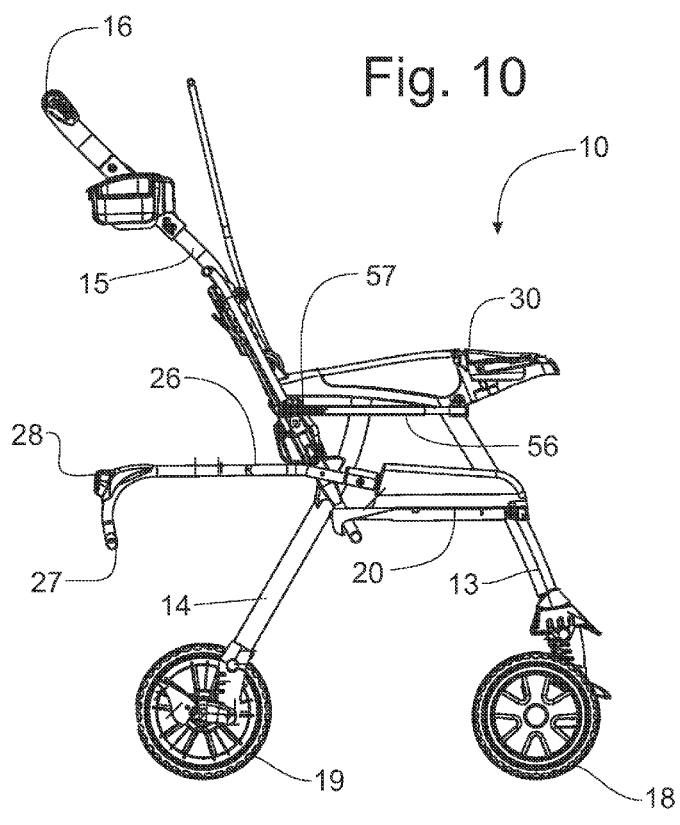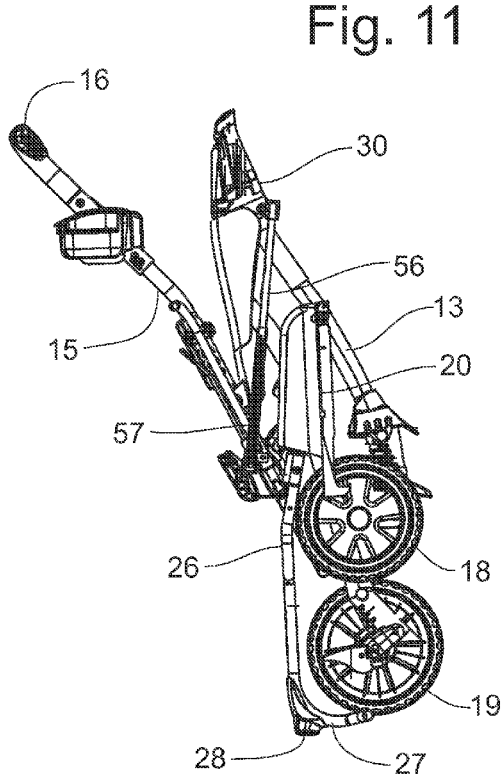

Fig. 17
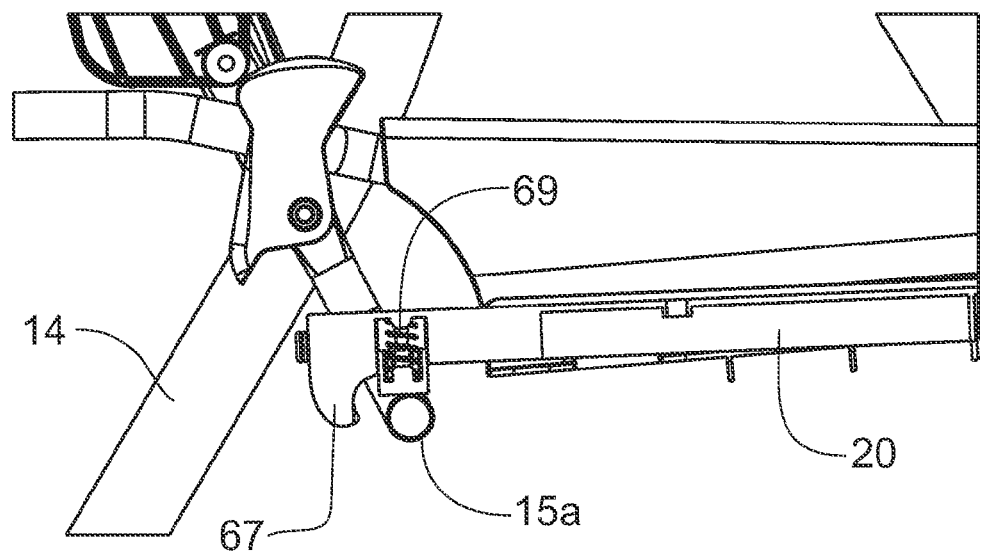
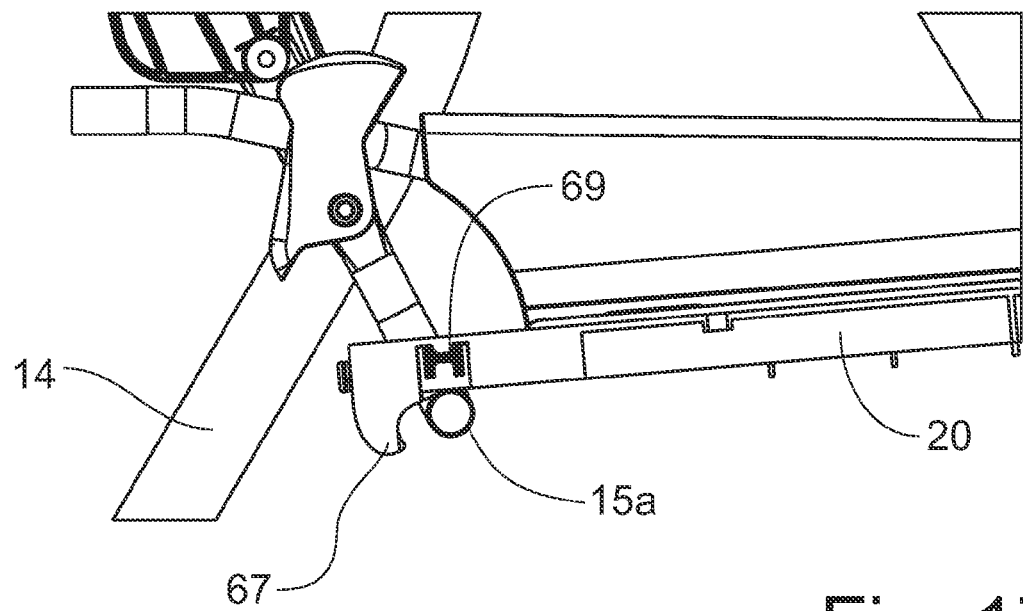
Fig. 17A

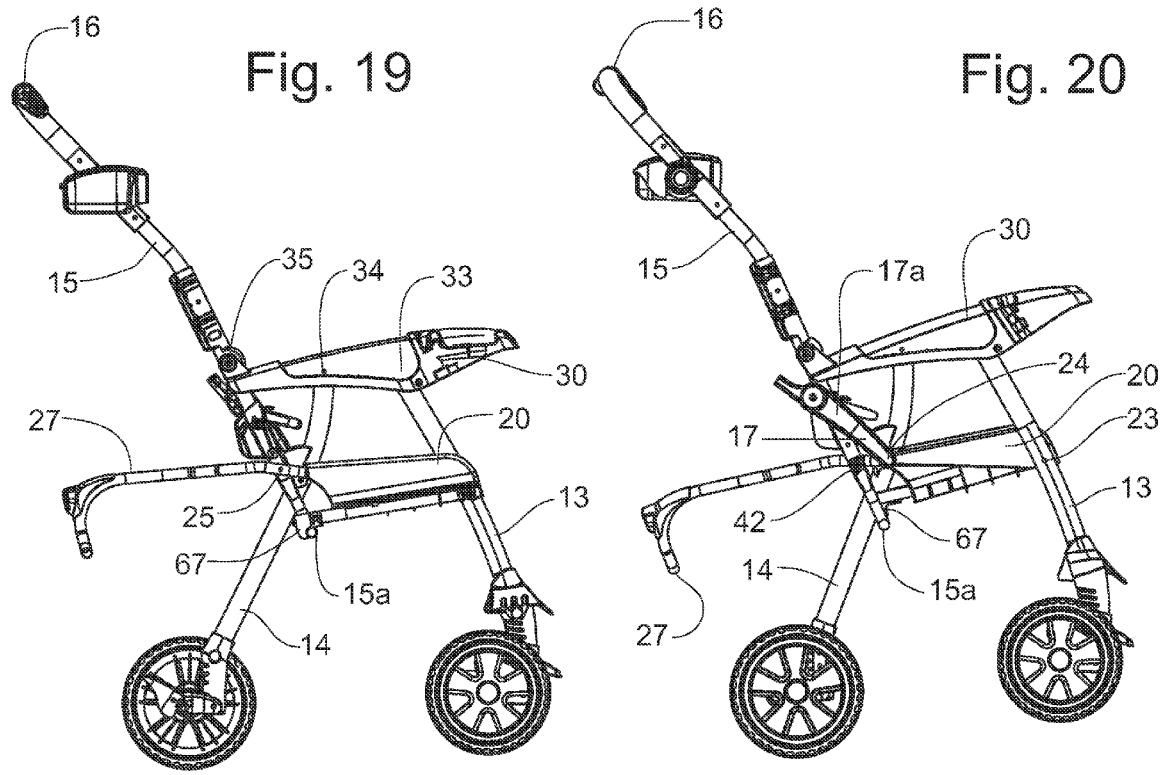

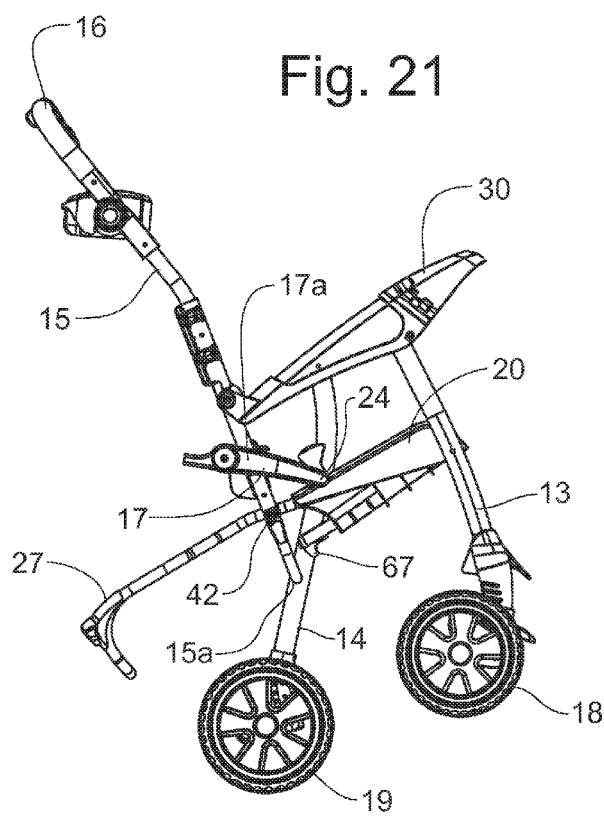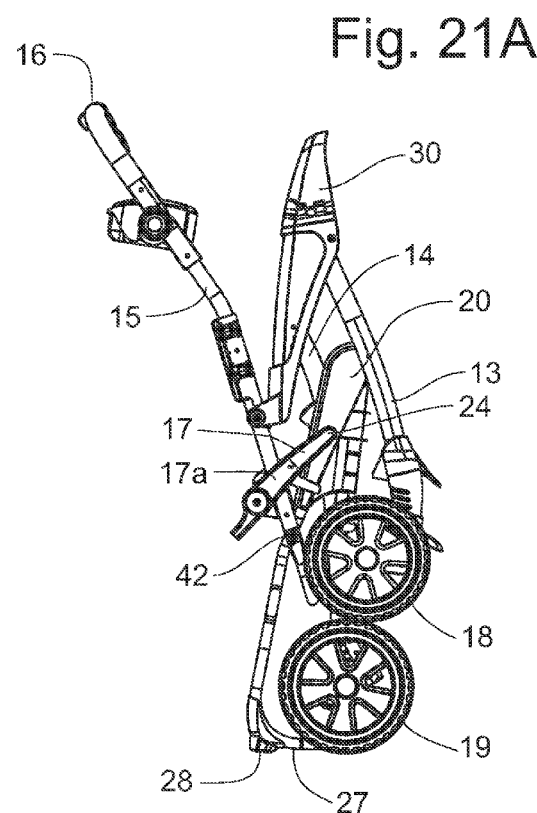

STROLLER WITH SPRING-ASSISTED FOLD MECHANISM

CROSS-REFERENCE TO RELATED APPLICATIONS

This application claims priority on U.S. Provisional Patent Application Ser. No. 60/800,572, filed on May 15, 2006; on U.S. Provisional Patent Application Ser. No. 60/833,433, filed on Jul. 26, 2006; on U.S. Provisional Patent Application Ser. No. 60/868,937, filed on Dec. 7, 2006; and on U.S. Provisional Patent Application Ser. No. 60/887,611, filed on Feb. 1, 2007; the contents of all four of these provisional patent applications being incorporated herein by reference.

FIELD OF THE INVENTION

The present invention relates generally to a stroller for use in transporting young children, and, more particularly, to a spring-powered assist mechanism for use in affecting a folding of the stroller into a compact transport configuration.

BACKGROUND OF THE INVENTION

Strollers for transporting young children are commercially available in many styles and configurations. Strollers are normally configurable in an operative position in which the child is placed on a seat forming part of the stroller to be transported from one place to another by a caregiver pushing the stroller manually, and in a compact storage configuration in which the stroller is folded into a position in which the frame is collapsed and is unusable for the normal function of transporting young children until the stroller is returned to the operative position. These strollers can be folded from the operative configuration into the storage configuration in a number of different ways to achieve a storable size for the stroller frame.

Known commercially available strollers can be very difficult to fold into the storage configuration. Many times, the caregiver needs to fold the stroller from the operative configuration into the storage configuration while holding the baby that was being transported in the stroller. To affect the folding of the stroller, the frame components are pivotally connected to one another and a latch mechanism that locks the frame members into an expanded configuration corresponding to the transport position. The latch mechanism is operatively controlled by a latch release apparatus that is often located near the center of the steering handle. The release mechanism can typically be activated using one hand, which is often referred to as a One Hand Fold Mechanism in the industry. Even with the one hand fold release mechanism located at a convenient location and being able to be activated by one hand, the person trying to collapse the stroller into the storage position will normally need to use his or her other hand to move the frame components and cause the stroller frame to fold into the storage position.

Complicating the folding of the stroller frame into a compact storage configuration, particularly when the caregiver is not yet familiar with the structure of the stroller, the different manufacturers and models of strollers utilize many different means of folding and unique folding geometries such that it is not always easy to understand how the stroller frame is to fold or even which direction the frame actually folds. For instance, some strollers fold by moving the steering handle up and toward the front of the stroller and other strollers fold by moving the steering handle down and toward the rear of the stroller. Many times, when a new user interacts with their stroller for the first time, they can activate the one hand release mechanism but then do not know which way to move the handle to initiate the folding process. Thus, folding the stroller is typically done by trial and error and usually requires the use of two hands.

One Hand Fold Mechanisms will typically provide an actuator that provides the caregiver with a large mechanical advantage when initiating the folding process. This extra leverage requires less grip force from the caregiver and, therefore, makes the activation of the folding process easier to accomplish. Additionally, a secondary lock mechanism is desirable to ensure that the folding mechanism remains deactivated until the caregiver consciously decides to activate it using two separate and distinct motions relating to the activation of the release mechanism. Even when the release mechanism and the secondary lock mechanism are provided for the folding apparatus of a stroller, an additional anti-fold latch corresponding to the presence of the child within the structure of the stroller can be desired to prevent the unintentional actuation of the folding apparatus whenever the child is still seated within the stroller.

In U.S. Pat. No. 3,873,116, issued on Mar. 25, 1975, to Gianluca Perego, a spring mechanism is utilized to bias the movement of a portion of the stroller toward a collapsed position; however, the entire collapsing of the stroller from the operative position to the storage position is not accomplished through this spring biasing mechanism. An auxiliary safety structure is disclosed for a child's stroller in U.S. Pat. No. 5,106,116, granted to Shum Chen on Apr. 21, 1992, whereby a spring-loaded block preventing the pivotal movement of the stroller frame is overcome by the weight of a child seated in the stroller to prevent the stroller from being collapsed when the child is seated in the stroller. Once the child is lifted out of the stroller seat, the spring releases the block from engagement with the corresponding frame member to allow pivotal movement thereof into the collapsed storage position. In U.S. Pat. No. 6,715,783, issued on Apr. 6, 2004, to Wayne Hanson, et al, a gas spring is utilized to lock the positions of pivotally connected stroller frame members so that the selected height of the seat can be secured.

Accordingly, it would be desirable to provide an improved stroller folding mechanism that will normally be operable through manipulation of the release mechanism whenever the child is not seated within the stroller structure.

SUMMARY OF THE INVENTION

It is an object of this invention to provide a spring-assisted fold mechanism for a stroller used for transporting children along the surface of the ground.

It is another object of this invention to provide a fold mechanism that can be powered by a spring mechanism to cause the stroller frame structure to fold automatically from the operative position when the release mechanism is properly actuated.

It is a feature of this invention that the spring mechanism can be a single gas spring located beneath the seat structure of the stroller.

It is another feature of this invention that the spring mechanism can be a torsion spring mounted on one frame component and operatively engaged with a second frame component that is pivotally connected with the first frame component to urge the pivotal movement of the two frame components into a folded configuration.

It is still another feature of this invention that the stroller frame components that are pivotally connected can be interconnected with a spring mechanism to urge the pivotal movement of the stroller frame components into a folded configuration.

It is an advantage of this invention that the stroller can be converted from an operative position to a folded condition simply through the actuation of a release mechanism.

It is another advantage of this invention that the stroller structure is spring-loaded for movement into a folded configuration.

It is still another advantage of this invention that the stroller will automatically move into the folded configuration whenever the latch mechanism restraining the pivotal movement of the stroller frame members is released.

It is still another feature of this invention that the stroller can be folded from an operative position to the folded configuration through manipulation with a single hand of the caregiver.

It is yet another feature of this invention that the stroller is provided with an anti-fold latch that prevents the stroller from being folded whenever a child is seated in the stroller.

It is yet another advantage of this invention that the anti-fold latch prevents the stroller from folding even when the release mechanism is activated, if a child is seated in the stroller.

It is a further feature of this invention that the anti-fold latch is spring-loaded into an inoperative position, but is movable into a locking position when the weight of a child placed into the seat of the stroller overcomes the spring biasing the anti-fold latch into the inoperative position.

It is yet another object of this invention to provide a spring-assisted fold mechanism for a stroller, which is durable in construction, inexpensive of manufacture, carefree of maintenance, facile in assemblage, and simple and effective in use.

It is yet another object of this invention to provide an anti-fold latch mechanism cooperable with a spring-assisted fold mechanism for a stroller to restrict operation thereof when a child is positioned on the stroller seat, which is durable in construction, inexpensive of manufacture, carefree of maintenance, facile in assemblage, and simple and effective in use.

These and other objects, features and advantages are accomplished according to the instant invention by providing a spring-assisted fold mechanism for a child's stroller that is operable to collapse the stroller frame into a storage configuration upon actuation of a release mechanism controlling the stroller fold latch mechanism. The stroller includes a spring device interconnecting two of the pivotally connected frame components to urge the pivotal movement thereof into a collapsed, folded configuration. An anti-fold latch mechanism is associated with the stroller seat to move from an inoperative position into a locking position whenever a child is placed into the stroller seat to prevent the fold mechanism from collapsing the frame of the stroller until the child is removed from the seat. The spring device can be configured as a gas spring, a torsion spring, a compression spring or an elastomeric member that can be stretched to exert a biasing force on the stroller frame to urge movement into the collapsed position.

BRIEF DESCRIPTION OF THE DRAWINGS

The advantages of this invention will be apparent upon consideration of the following detailed disclosure of the invention, especially when taken in conjunction with the accompanying drawings wherein:

FIG. 7 is an enlarged partial cross-sectional view showing the spring-assisted fold mechanism that can be utilized in either embodiment, corresponding to lines 7-7 of FIG. 1;

FIG. 8 is an enlarged partial cross-sectional view showing the spring-assisted fold mechanism similar to that of FIG. 7, but corresponding to lines 8-8 of FIG. 1;

FIG. 10 is a cross-sectional view taken through the center of the stroller corresponding to lines 10-10 of FIG. 3 to show a side elevational view of an alternative side mounted compression spring device operable to power the folding of the stroller;

FIG. 11 is a cross-sectional view similar to that of FIG. 10 to show a side elevational view of the stroller depicted in FIG. 10, but in the folded configuration with the compression spring device expanded;

FIG. 17 is an enlarged partial side elevational view of an alternative spring biasing mechanism for the anti-fold latch mechanism depicted in FIG. 16 with the spring urging the anti-fold latch mechanism into an unlocked position;

FIG. 17A is an enlarged partial side elevational view of the anti-fold latch mechanism similar to that of FIG. 17A, but with the spring compressed to correspond to the presence of a child in the stroller seat and, thereby, locking the pivotal movement of the stroller frame;

FIG. 19 is a schematic cross-sectional view of the stroller frame shown in FIG. 18, but with the frame starting the fold sequence while the anti-fold latch mechanism is in the latched position;

FIG. 20 is a schematic cross-sectional view of the stroller frame of FIG. 18 in an initial phase of the folding sequence with the anti-fold latch being cleared to allow the folding to continue under power of the spring-assisted fold mechanism;

FIG. 21 is a schematic cross-sectional view of the stroller frame of FIG. 18 approximately midway through the fold process;

FIG. 21A is a schematic cross-sectional view of the stroller frame of FIG. 18 compactly folded into the storage position by the spring-assisted fold mechanism;

DETAILED DESCRIPTION OF THE PREFERRED EMBODIMENT

Figure 6:
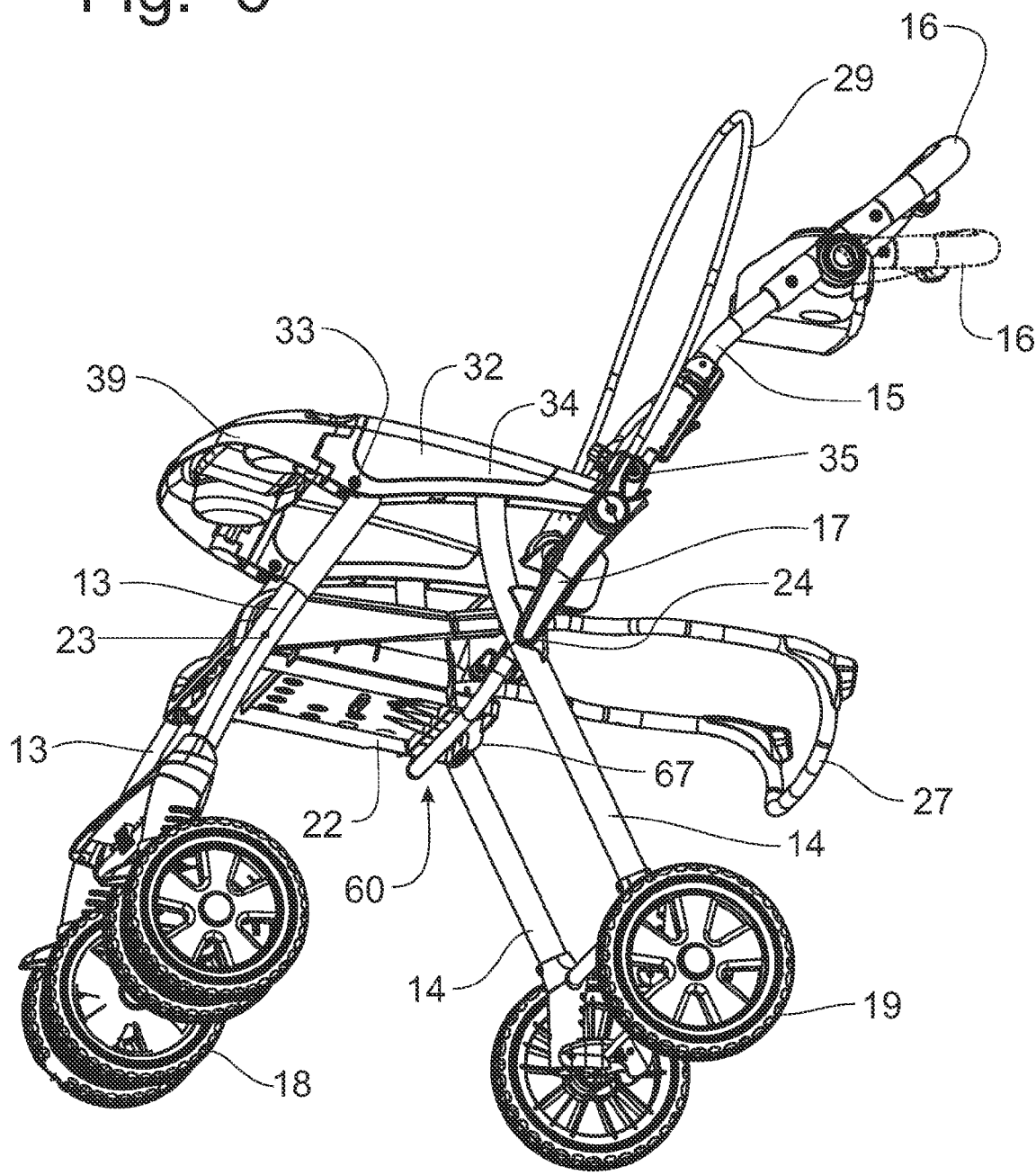
FIG. 6 is a lower, left perspective view of the stroller depicted in FIG. 4.

Referring now to FIGS. 1-6, a stroller incorporating the principles of the instant invention can best be seen. The stroller 10 includes a wheeled frame 12 that is supported on front and rear ground-engaging wheels 18, 19 that permit mobile movement of the stroller 10 over the surface of the ground to transport children. The frame 12 includes a pair of transversely spaced front legs 13 on which the front wheels 18 are mounted and a corresponding pair of transversely spaced rear legs 14 on which the rear wheels 19 are mounted. The frame also includes a pair of upwardly extending, transversely spaced handle tubes 15 terminating in a handle bar 16 defining a preferred generally inverted U-shaped configuration. As is best seen in FIG. 6, the handle bar 16 is preferably positionally adjustable about a pivot axis corresponding to the mounting of the cup holder. Interconnecting the front and rear legs 13, 14 and the handle tubes 15 in a manner described in greater detail below are generally horizontally oriented seat assembly 20 and an arm rest and tray assembly 30.

The front legs 13 are pivotally connected to the arm rest assembly 30 about a first pivot 33, while the rear legs 14 are pivotally connected to the arm rest assembly 30 about a second pivot 34 spaced rearwardly of the first pivot 33. Additionally, the front legs 13 are pivotally connected to the seat assembly 20 about a first seat pivot 23. Furthermore, the arm rest assembly 30 is pivotally connected to the handle tubes 15 about a third pivot 35 and the seat assembly 20 is pivotally connected to the handle tubes about a second seat pivot 25 that is located along the handle tubes 15 below the third arm rest pivot 35.

The handle tubes 15 are articulated about an articulation pivot axis 17a to a lower stabilization member 17, which is pivotally connected to the rear legs 14 about a pivot 24. The handle tubes 15 are provided with a latch mechanism 40 that includes retractable latch members 42 housed within the handle tubes 15 to lock the handle tubes 15 to the corresponding rear leg 14 in an upright orientation. The retraction of the latch members 42 allow an articulation of the handle tubes 15 relative to the stabilization members 17, as will be described in greater detail below, to accomplish a folding of the stroller frame 12 into a compact storage configuration. The movement of the latch members 42 is controlled by a latch actuation mechanism 45 located in the handle bar 16.

Figure 1:
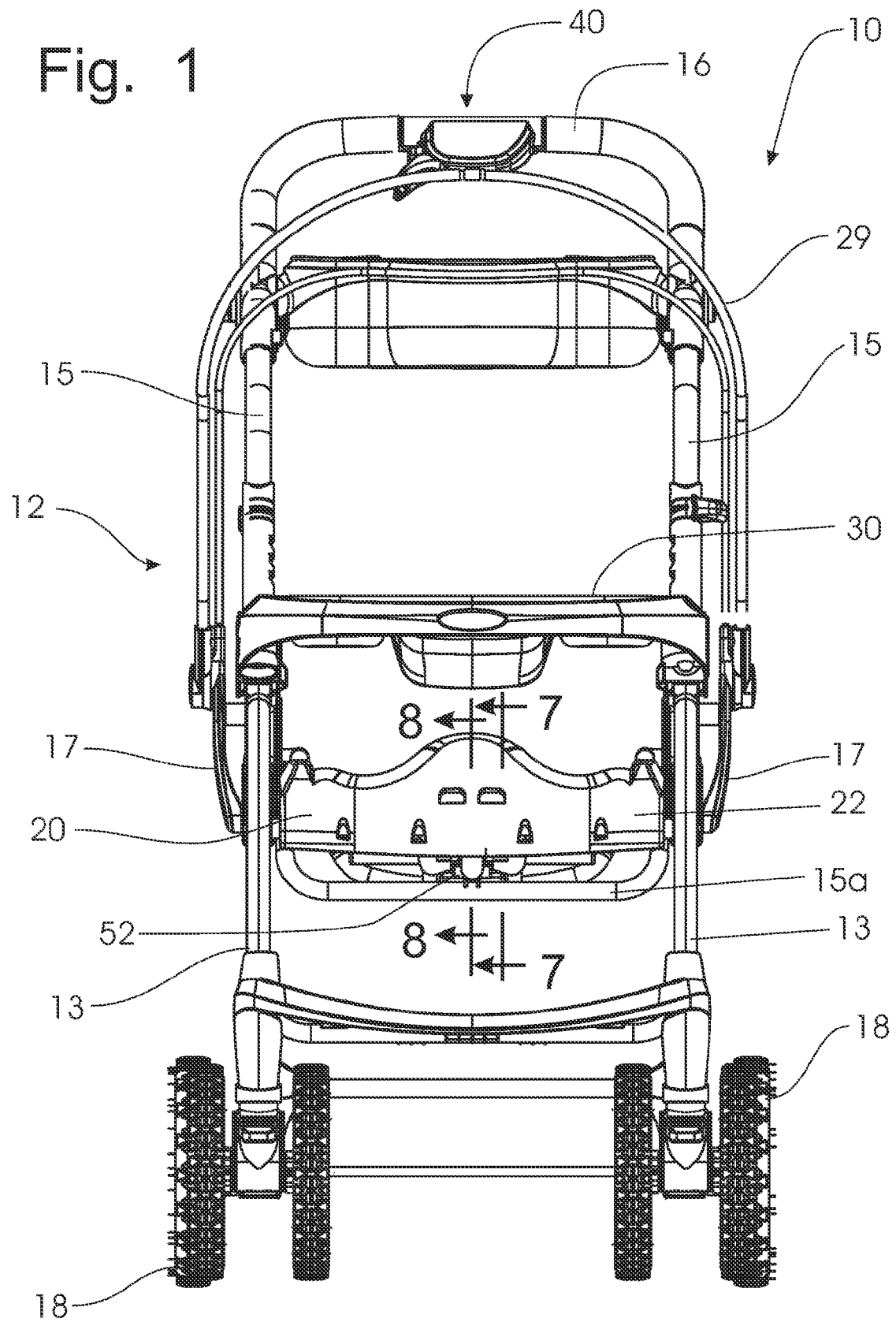
FIG. 1 is a front elevational view of a first embodiment of a stroller incorporating the principles of the instant invention, the conventional fabric portions of the stroller forming the seat cushion, hood and other non-frame components of the stroller being removed for purposes of clarity.
Figure 2:
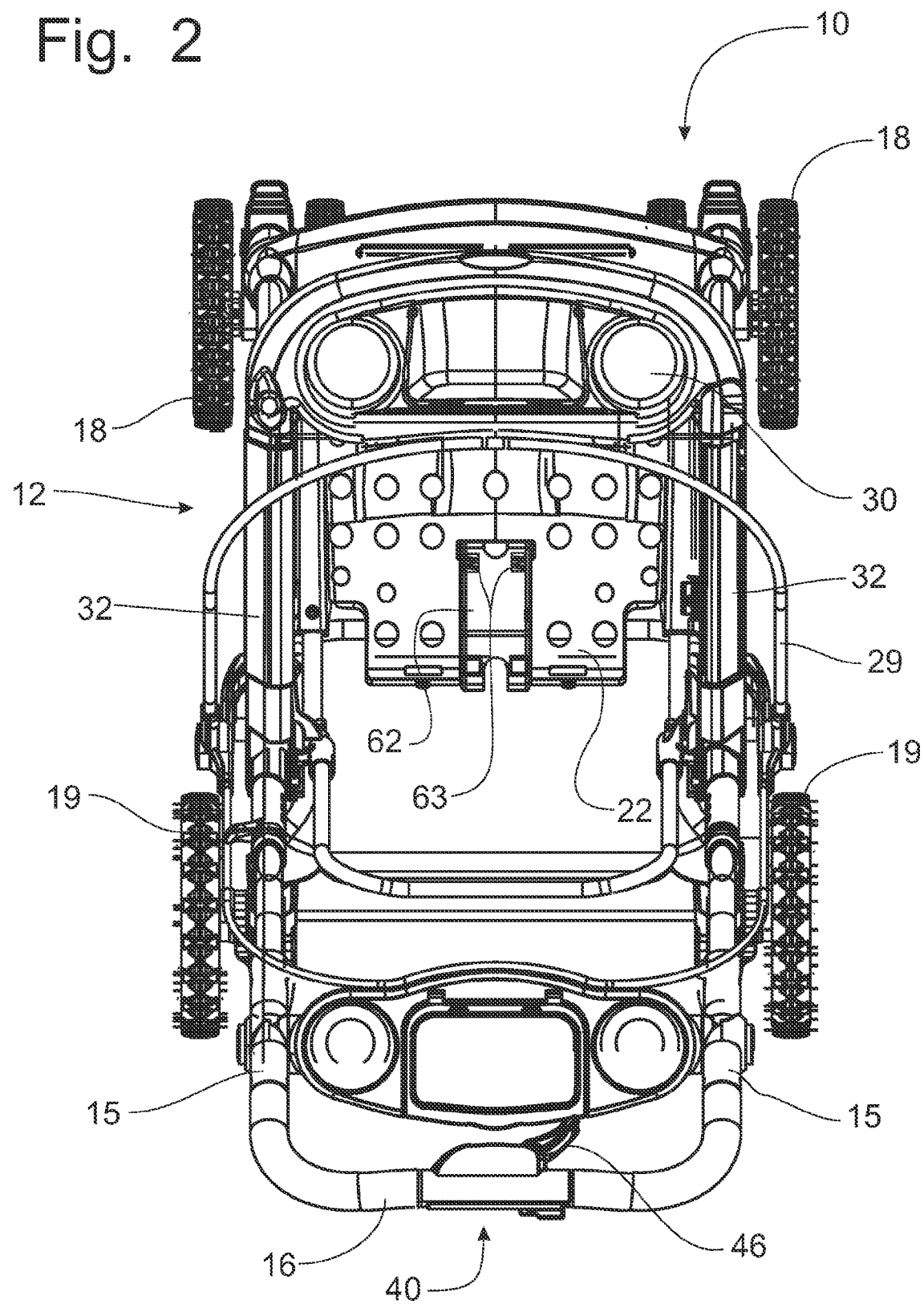
FIG. 2 is a top plan view of the stroller shown in FIG. 1.
Figure 3:
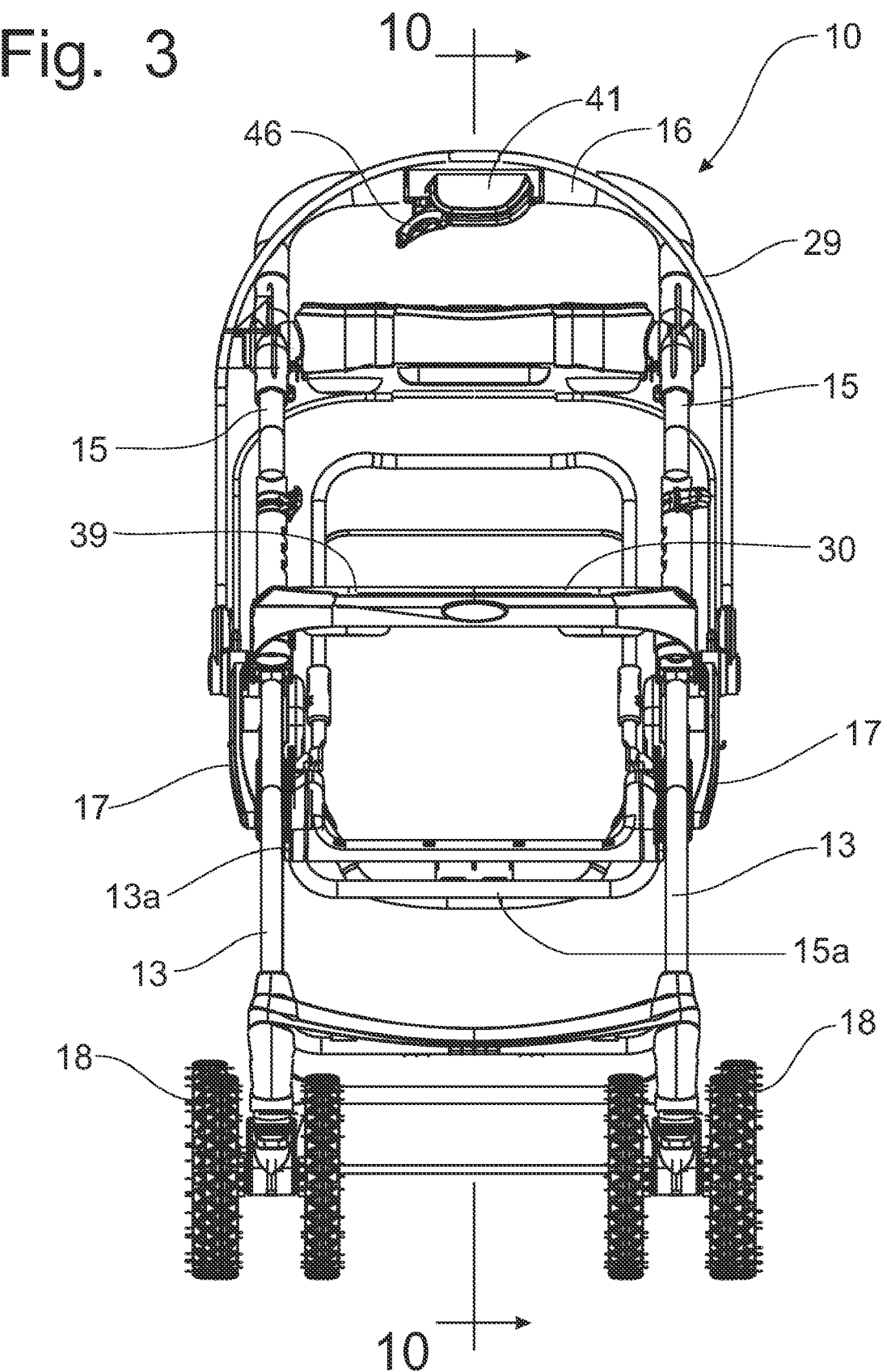
FIG. 3 is a front elevational view of a second embodiment of a stroller incorporating the principles of the instant invention, as with FIG. 1, the conventional fabric portions of the stroller forming the seat cushion, hood and other non-frame components of the stroller being removed for purposes of clarity, the spring apparatus powering the folding of the stroller frame being removed for purposes of clarity.
Figure 4:
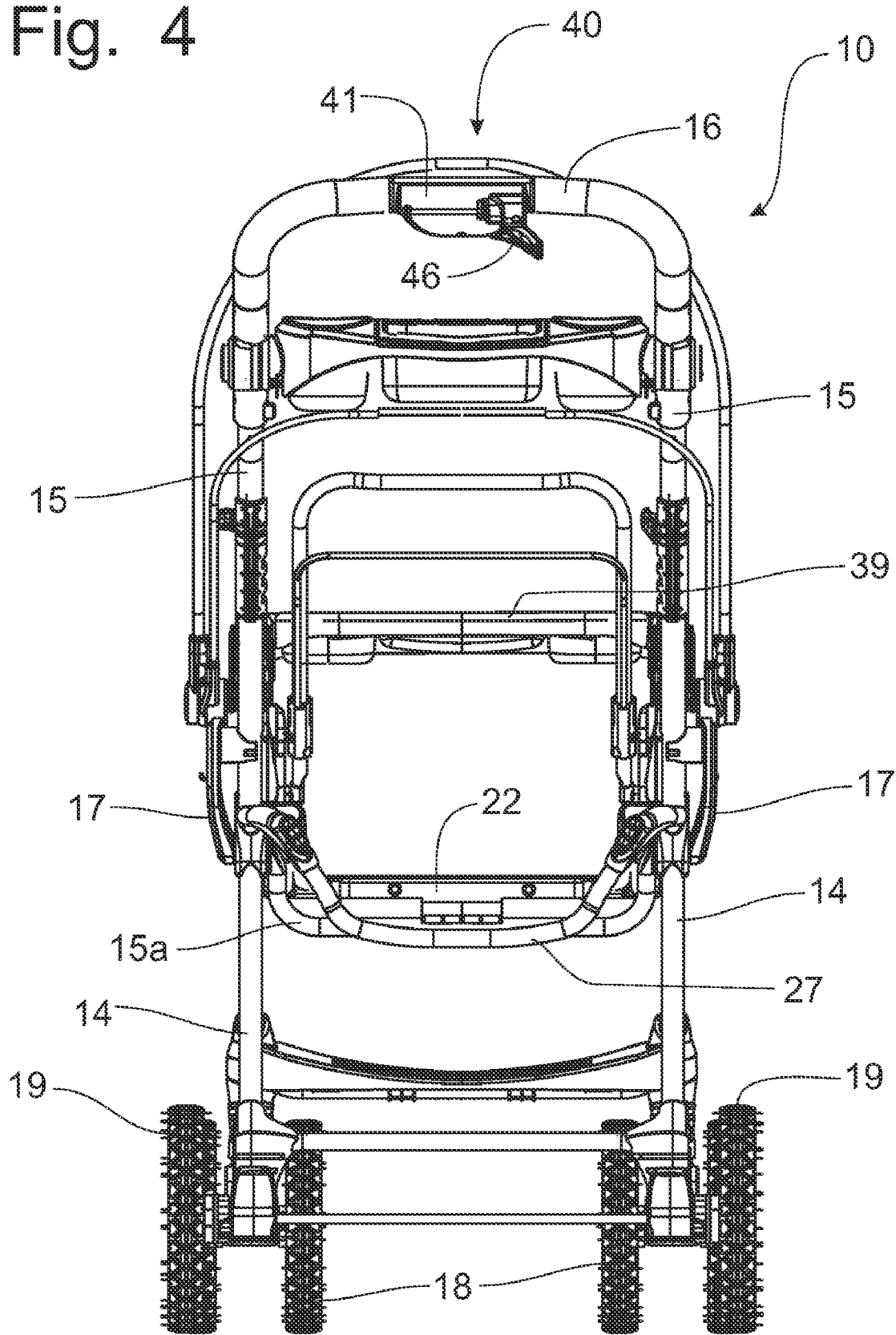
FIG. 4 is a rear elevational view of the stroller depicted in FIG. 3.
Figure 5:
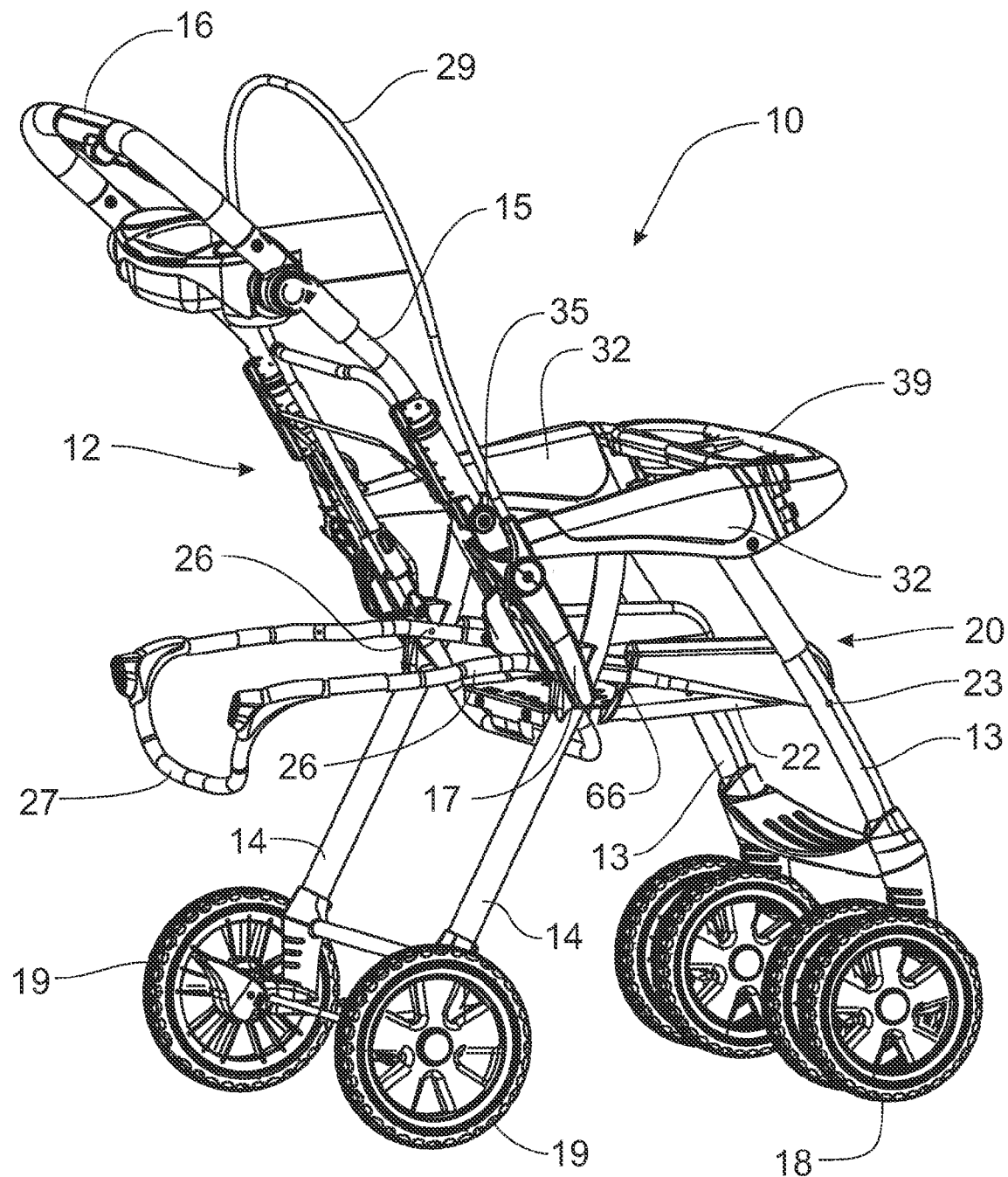
FIG. 5 is a right, rear perspective view of the stroller depicted in FIG. 4.

The seat assembly 20 is formed with a seat pan 22 that can be in a formed shape as depicted in FIGS. 1 and 2, or in a generally planar configuration as is depicted in FIGS. 3-6. One of the differences between the shape of the seat pan 22 in FIG. 1 and in FIG. 3 is the formation of the seat to conform to a ASTM standard that either prevents a child from passing between the seat 22 and the tray 39, or allows the entire body of the child to pass between the seat 22 and the tray 39. Projecting rearwardly from the seat pan 22 is a pair of transversely spaced seat tubes 26 that support the seat pan 22 and connect with a basket tube 27 that continues rearwardly from the seat tubes 26 to provide support for a basket (not shown) in which loose items can be stored when the stroller 10 is in the operative configuration.

The arm rest assembly 30 is formed with a pair of transversely spaced arm rests 32 interconnected at the forward ends thereof by a tray 39 that is pivotally connected to one of the arm rests 32 and latched to the opposing arm rest 32 such that the tray 39 can be disconnected from the latched arm rest 32 and pivoted about the other arm rest 32 to permit access into the seat assembly 20 onto which a child can be seated. One of ordinary skill in the art will recognize that the stroller frame 12 is depicted in FIGS. 1-6, and in other figures as well, without the fabric and padding, commonly referred to as the soft goods, which is mounted on the frame 12 to provide an aesthetically pleasing and comfortable stroller 10 on which a child can be transported from place to place. For example, in some of the figures, the canopy hoop 29 is depicted on which a canopy cover (not shown) is attached to form a cover that extends over the child positioned in the seat 22, the canopy hoop being pivotably connected to the handle tubes 15 or stabilizer members 17 to move between a retracted position adjacent the handle tubes 15 and a lowered position adjacent the arm rests 32.

Referring now to FIGS. 18-21A, the folding process of the stroller 10 can best be seen. The latch members 42 when extended into the rear legs 14 from the handle tubes 15 prevent the articulation of the handle tubes 15 and, thereby, lock the stroller frame 12 in the operative position shown in FIG. 18. With the handle tubes 15 locked against articulation, the frame components are not able to pivot relative to one another. When the latch members 42 are withdrawn from the rear legs 14, the articulation of the handle tubes 15 allows the front leg 13 to pivot relative to the seat assembly 20 and the arm rest assembly 30, while the articulating handle tubes 15 lower the rearward end of the arm rest assembly 30 toward the seat assembly 20, which in turn pivots about the pivot 25 to allow the entire frame 12 to collapse into the storage configuration depicted in FIG. 21A.

Returning to FIGS. 1-8, a first embodiment of a spring assist mechanism 50 can best be seen. The spring assist mechanism 50 can take the form of a gas spring 52 that is pivotally connected to a front cross member 13a corresponding to the first seat pivot 23 and extending transversely between the front legs 13. The gas spring 52 is preferably centrally located and extends rearwardly from the front cross member 13a for pivotally connection with a rear cross member 15a extending transversely between the handle tubes 15. The gas spring 52 is arranged to exert a biasing force that urges the front and rear cross members 13a, 15a, apart. So long as the latch members 42 are engaged with the rear legs 14, the biasing force exerted by the gas spring 52 is resisted and the stroller remains in the expanded operative configuration. When the latch mechanism 40 releases the handle tubes for articulation, the spring force exerted by the gas spring 52 pushes the two cross members 13a, 15a apart to affect the folding of the frame 12, as described above. With reference to FIGS. 18-21A, one skilled in the art will note that the front and rear cross members 13a, 15a spread apart during the folding process. Thus, the spring force exerted by the gas spring 52 will be operable to drive the folding process from the operative configuration to the storage configuration.

Figure 9:
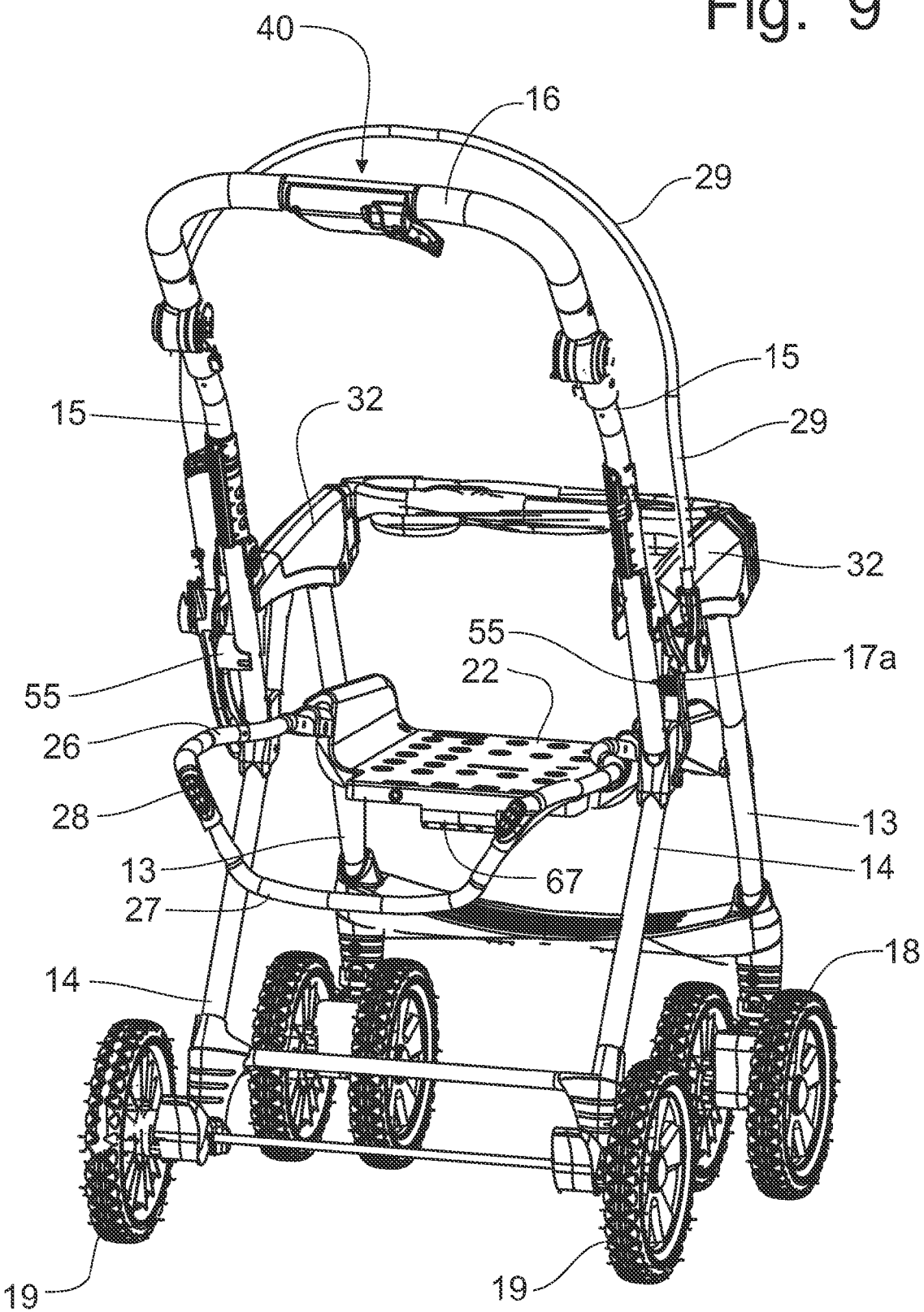
FIG. 9 is a rear perspective view of a stroller utilizing a torsion spring interconnecting pivotally connected frame members to power the folding of the stroller frame.

As can be seen in FIG. 9, the spring force can be exerted by a torsion spring 55 located at the articulation pivot 17a, through preferably a torsion spring 55 on each side of the frame 12. Spring force is stored in the torsion spring 55 when the frame 12 is placed into the operative configuration and the handle tubes 15 are locked into engagement with the rear legs 14 by the latch members 42. The release of the latch members 42, as described above, permits articulation of the handle tubes 15 and the stabilizer members 17 which is powered by the spring force in the torsion spring 55.

Yet another embodiment of the spring assist mechanism 50 can be seen in FIGS. 10 and 11 in which a pair of laterally spaced telescopic tubular members 56, each containing a compression spring 57, is mounted at the first pivot 33 and extends rearwardly to connect with the corresponding handle tube 15 at or near the articulation pivot 17a. When the latch mechanism 40 releases to allow the frame 12 to fold the spring force stored in the compressed spring 57 pushes the handle tubes 15 through the articulation that accompanies the folding process of the frame 12.

Figure 12:
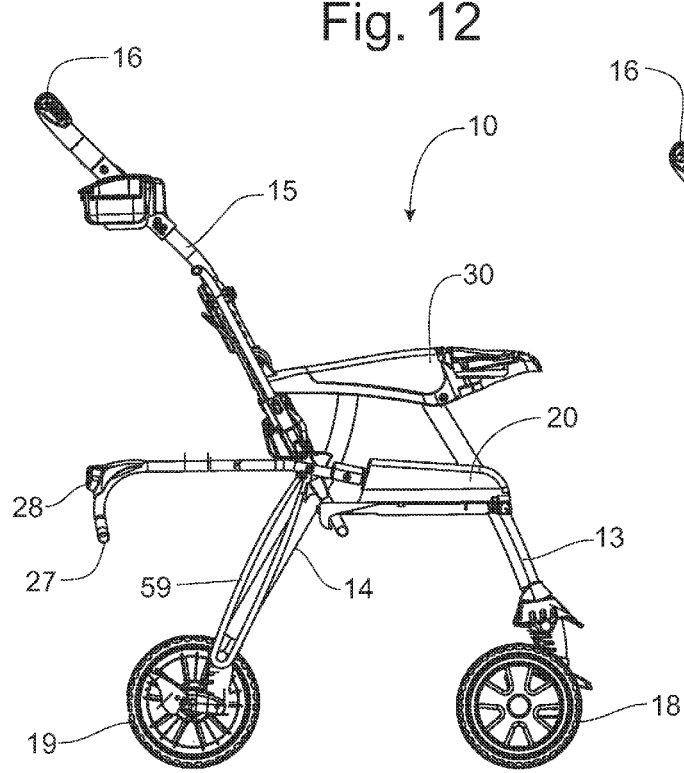
FIG. 12 is a cross-sectional view taken through the center of the stroller similar to that of FIG. 10 to show a side elevational view of an alternative elastomeric cord stretched to provide an operative spring force for folding the stroller frame.
Figure 13:
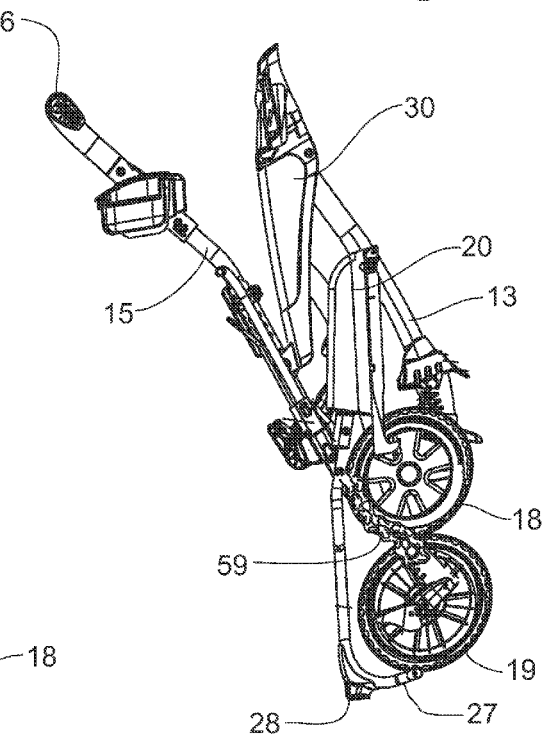
FIG. 13 is a cross-sectional view similar to that of FIG. 11, but showing the alternative elastomeric cord used to power the automatic folding of the stroller frame in a relaxed condition.
Figure 14:
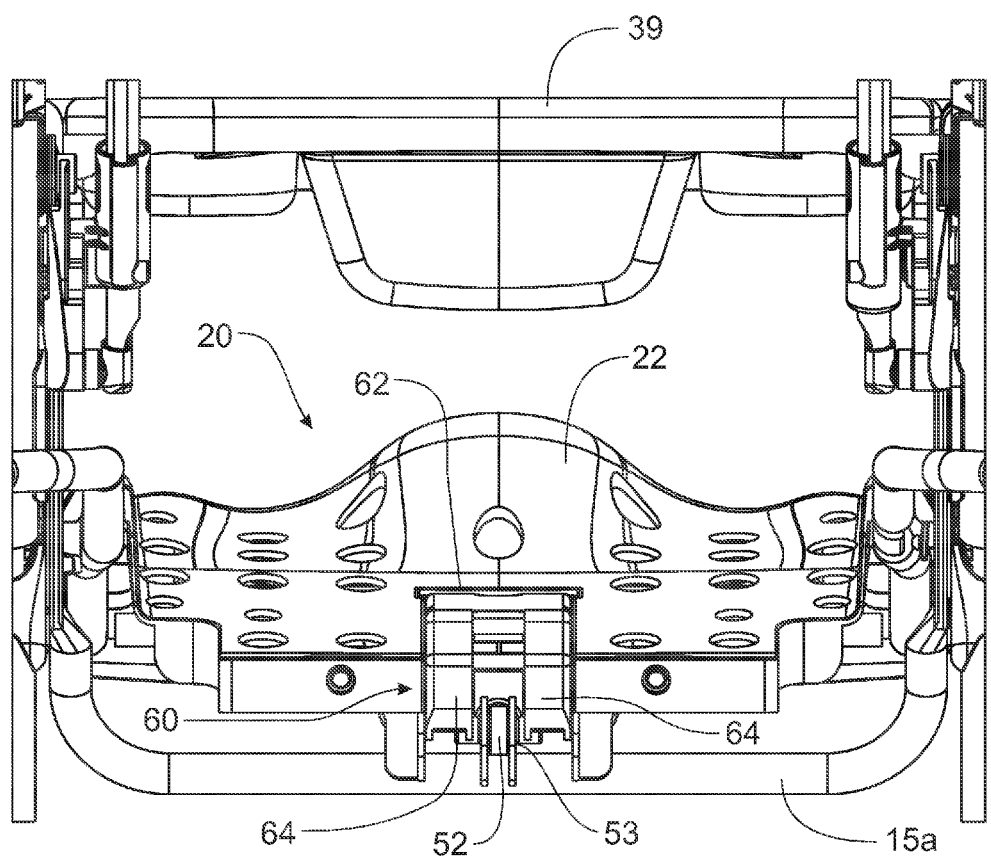
FIG. 14 is an enlarged rear elevational view of the seat portion of the stroller depicted in FIG. 1 to show the anti-fold latch mechanism.
Figure 15:
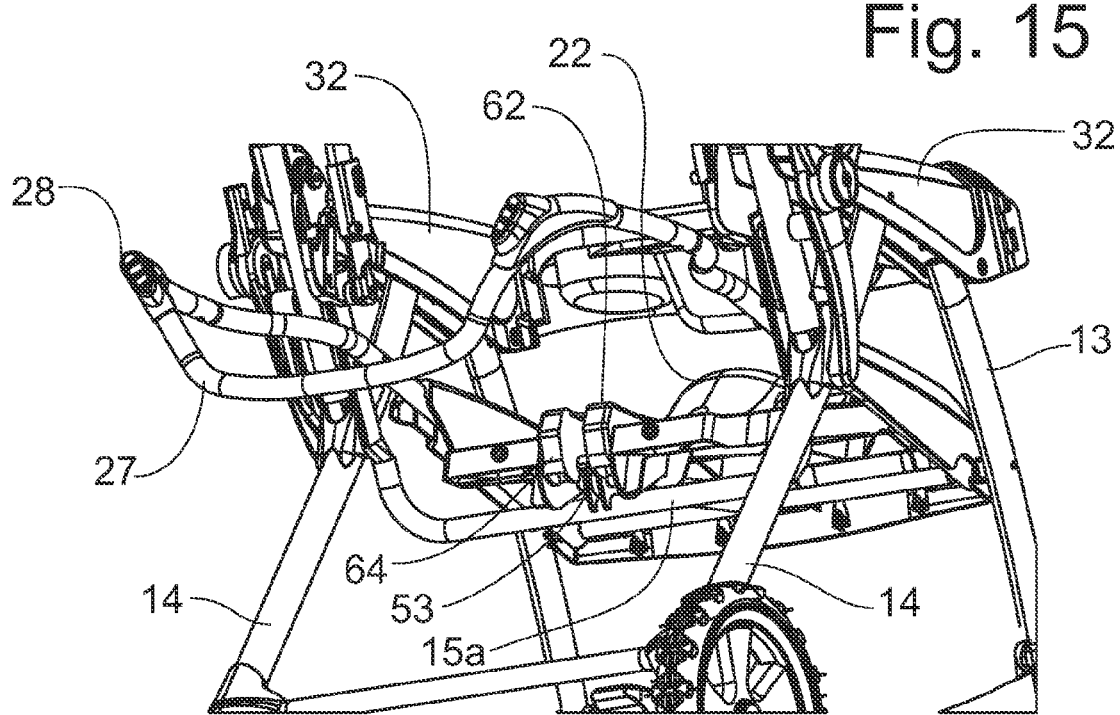
FIG. 15 is an enlarged rear perspective view of the anti-fold latch mechanism shown in FIG. 14 and positioned in the unlatched position.
Figure 15A:
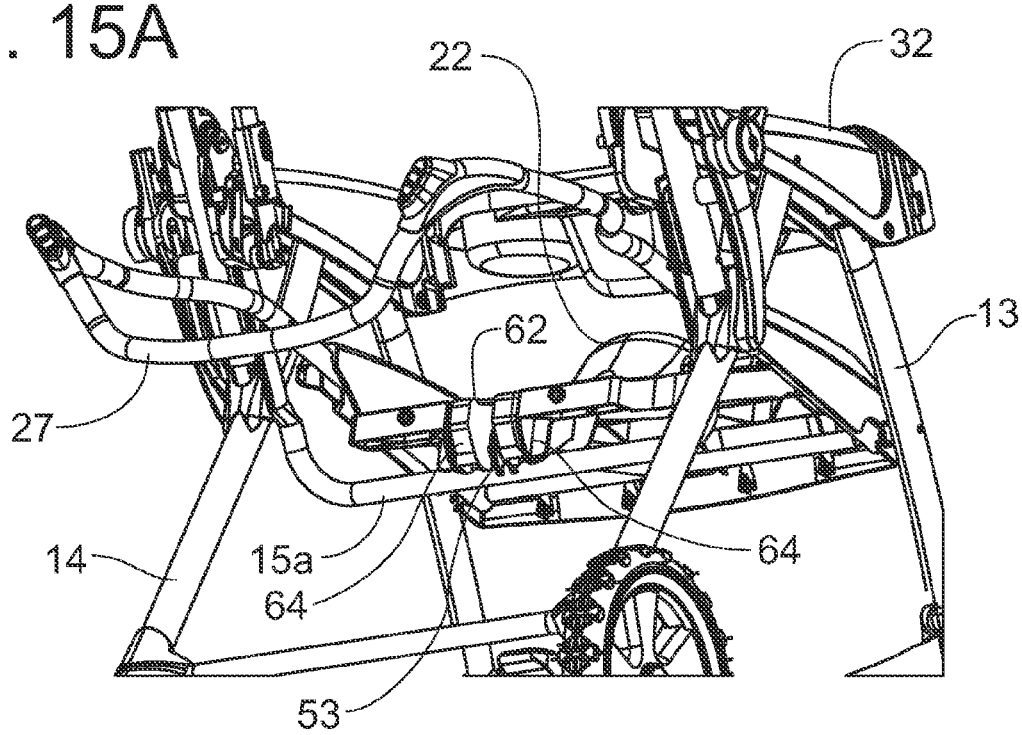
FIG. 15A is an enlarged rear perspective view of the anti-fold latch similar to that of FIG. 15 but moved into the latch position to prevent the folding of the stroller frame.

As can be seen in FIGS. 12 and 13, the spring force needed to convert the stroller frame 12 from the operative configuration into the folded storage configuration can be provided by elastomeric members 59, such as bungee cords, that are anchored at the distal end of the rear legs 14 near the rear wheels 19 and stretched to engaged the handle tubes 15, preferably at the articulation pivot 17a. Thus, when the latch mechanism 40 is released, the spring force stored in the stretched elastomeric members 59 pull the articulation pivot 17a toward the rear wheels 19, causing the articulation of the handle tubes 15 with respect to the stabilization members 17 to affect the folding of the stroller frame 12 into the compact storage configuration, as seen in FIG. 13, where the elastomeric member 59 is depicted in a relaxed state.

Referring now to FIGS. 1, 2 and 14-15A, a first embodiment of an anti-fold latch mechanism 60 can best be seen. The anti-fold latch mechanism 60 includes a spring-loaded trap member 62 that is centrally located at the rear of the seat pan 22. Preferably, the trap member 62 is pivotally supported on the seat pan 22 and includes a compression spring 63 that urges the trap member 62 upwardly. The trap member 62 preferably includes a pair of hook members 64 extending downwardly to be engagable with the mounting bracket 53 connecting the gas spring 52 to the rear cross member 15a, or with the rear cross member 15a itself, when the trap member is depressed against the biasing force of the compression spring 63. Thus, when a child is seated on the seat pan 22, the weight of the child overcomes the biasing force of the compression spring 63 and allows the trap member to depress to the level of the seat pan 22. At this point, the hook members 64 are in a position that interferes with the movement of the rear cross member 15a rearwardly, as occurs whenever the frame 12 starts the folding process. Accordingly, when a child is seated in the seat pan 22, the hook members 64 restrain the rear cross member 15a from moving away from the front cross member 13a, thus preventing the frame 12 from folding.

Figure 16:
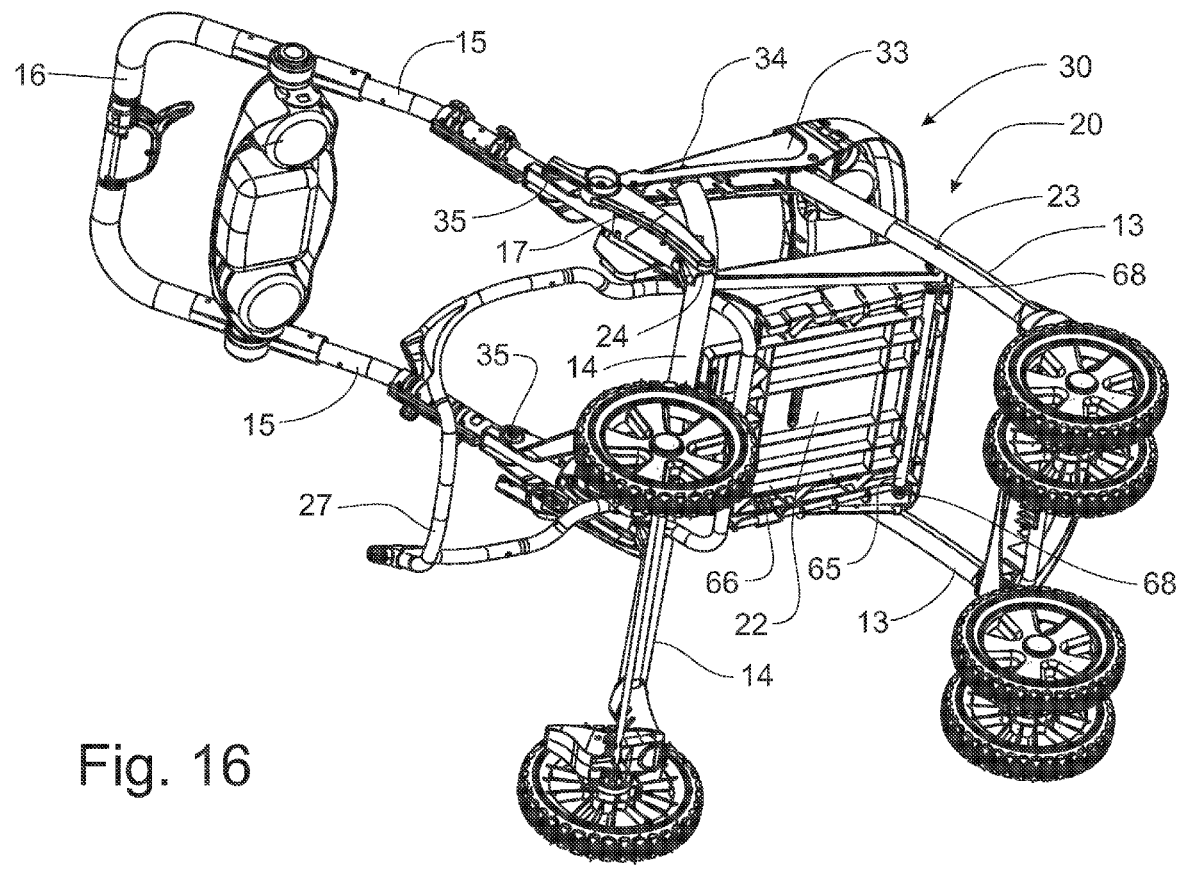
FIG. 16 is an enlarged perspective view of the stroller seat of the embodiment shown in FIG. 3 depicting the anti-fold latch mechanism associated with that embodiment, the upward biasing of the seat being provided by a torsion spring at the seat pivot axis.

A different embodiment for the anti-fold latch mechanism 60 is depicted in FIGS. 3-6, 9-13, and 16-21A. In this embodiment, the seat pan 22 is pivoted along a pivot axis 65 at the forward end of the seat pan 22 and is spring-loaded upwardly away from engagement with the rear cross member 15a. Preferably a stop 66 is provided on the seat pan 22 to engage other frame structure, such as the arm rest 32, to limit the upward pivotal movement of the seat pan 22 about the pivot axis 65. The spring force biasing the seat pan 22 upwardly could be provided by a torsion spring 68 mounted at the pivot axis 65, as depicted in FIG. 16, or preferably by a compression spring 69 seated at the rearward end of the seat pan to be engagable with the rear cross member 15a. Thus, when a child is seated on the seat pan 22, the biasing force exerted by the spring 68 or 69 is overcome and the seat pan 22 moves downwardly into engagement with the rear cross bar 15a. The hook members 67 preferably built into the rear portion of the seat pan 22 are then positioned to interfere with the rearward movement of the rear cross member 15a away from the front cross member 13a, which accompanies the folding process. Accordingly, when a child is seated on the seat pan 22, the hook members 67 prevent the stroller frame 12 from folding into the compact storage configuration.

The latch mechanism 40 for controlling the initiation of the folding operation described above can best be seen in FIGS. 2, 4 and 22-24C. The latch actuation mechanism 45 is located at the center of the handle bar 16 so as to be easily accessible by the caregiver operating the stroller 10. The primary actuation device is a lever 46 that is attached to or formed as a part of a first gear 47 rotatably mounted about a generally vertical axis of rotation within the housing 41. The first gear 47 is operably engaged with a second gear 47a which is also rotatably supported in the housing 41 for rotation about a second generally vertical axis of rotation spaced laterally from the first axis of rotation.

Figure 24A:
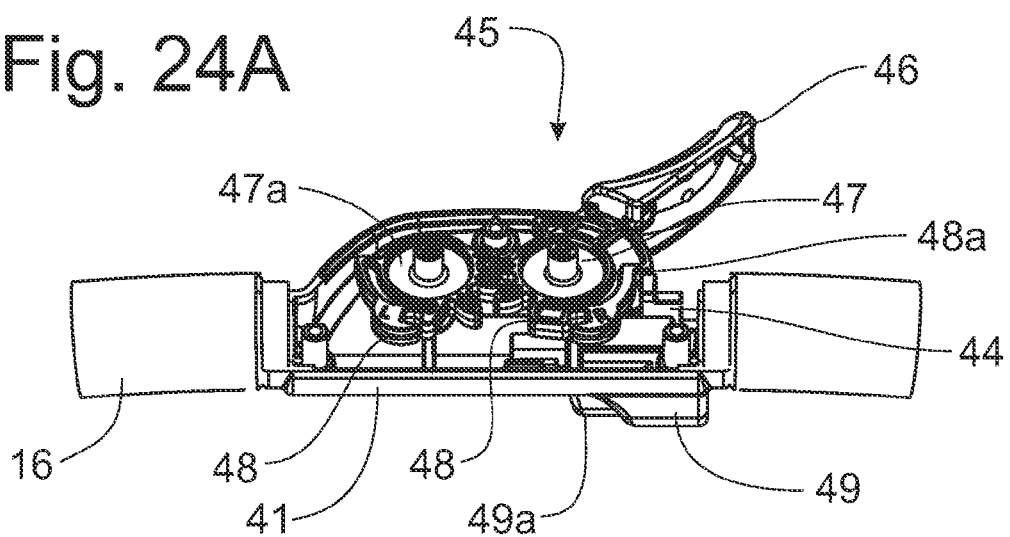
FIG. 24A is an enlarged partial elevational view of the fold actuator mechanism with the top cover broken away to view the internal gear actuators and the operation of the secondary latch mechanism, which is positioned to interfere with the operation of the fold actuation mechanism.
Figure 24B:
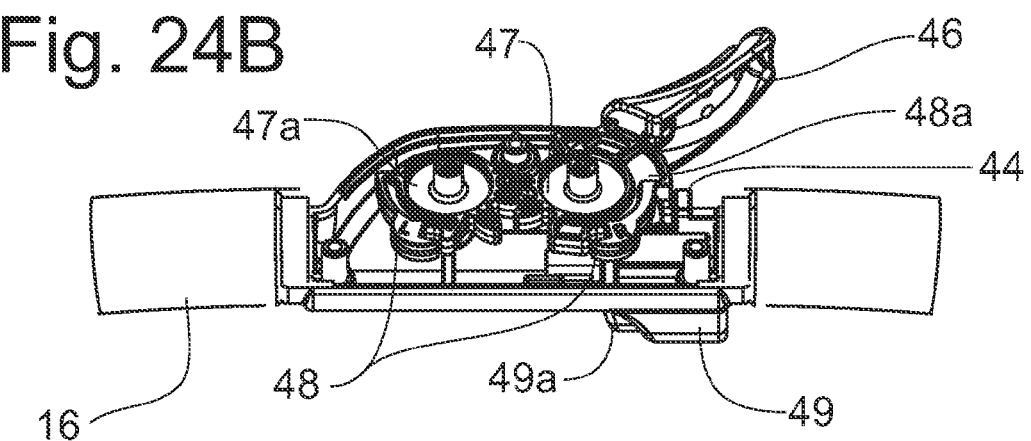
FIG. 24B is an enlarged partial elevational view of the fold actuation mechanism similar to that of FIG. 24A, but showing the selective movement of the secondary latch mechanism to allow manipulation of the fold actuation mechanism.
Figure 24C:
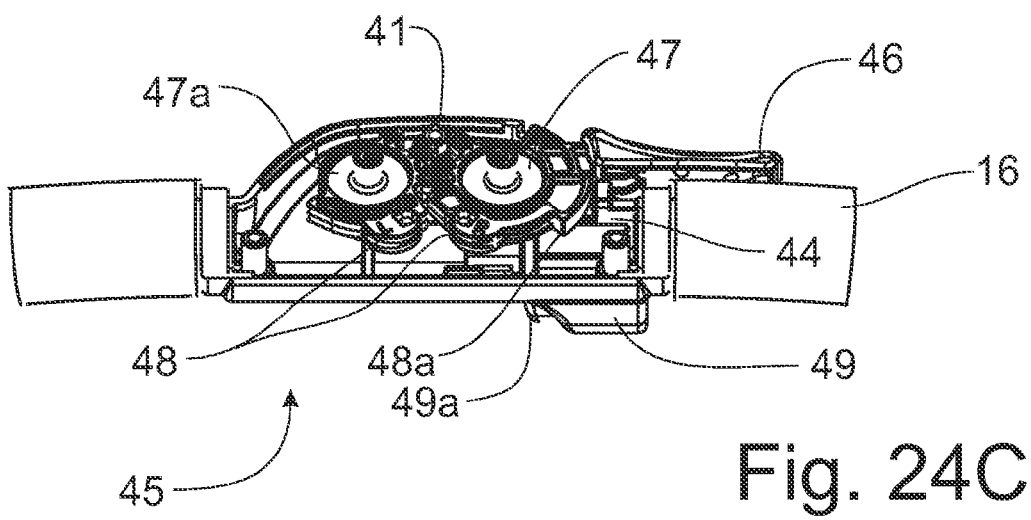
FIG. 24C is an enlarged partial elevational view of the fold actuation mechanism similar to that of FIG. 24B, but showing the subsequent movement of the fold actuation mechanism to release the stroller frame for folding into the storage position.

The first and second gears 47, 47a are arranged so that a pulling of the lever 46 toward the handle bar 16 causes a rotation of the first gear 47 and a resultant rotation of the second gear 47a to move connection tabs 48 inwardly toward the center of the handle bar 16, as can be seen in FIGS. 24B and 24C. Cables (not shown) are connected to each respective connection tab 48 and extend through the handle bar 16 and the corresponding handle tube 15 to reach the latch member 42. Thus, the pulling of the lever 46 against the handle bar 16, as depicted in FIG. 24C causes a retraction of the latch members 42 from the rear legs 14 into the handle tubes 15 to initiate the folding process described above. The utilization of a trigger-like lever 46 to provide the primary actuation motion for the latch mechanism 40 provides a force multiplier that known latch mechanisms do not provide. As a result, the latch mechanism 40 is more user friendly and the caregiver does not have to struggle to provide sufficient force to cause the latch members 42 to retract into the handle tubes 16 due to the binding forces exerted at the articulation pivot 17a by the spring assist mechanism 50.

To prevent an accidental actuation of the latch mechanism 40 due to an inadvertent grasping of the lever 46, a secondary latch 49 is incorporated into the latch actuation mechanism 45. The secondary latch 49 is preferably in the form of a button 49*a* having a spring 43 captured within the housing 41 to urge the button 49*a* outwardly from the housing 41. The button 49*a* is formed with a protrusion 44 that is movable with the button 49*a* from an interference position shown in FIG. 24A to an unlocking position shown in FIG. 24B. The protrusion 44 is engagable with an abutment 48*a* formed in the first gear 47 when in the interference position such that the first gear 47 cannot rotate until the protrusion 44 is moved into the unlocking, or non-interfering position. Accordingly, if the secondary latch 49 has not been actuated by depressing the button 49*a* into the housing 41, the lever 46 cannot be moved toward the handle bar 16 to initiate the folding process.

One skilled in the art will recognize that other configurations for the secondary latch would also be effectively operable, such as a pivoted lever (not shown) that would pivotally, rather than slidingly, move the protrusion out of interference with the abutment 48*a* on the first gear. Furthermore, one skilled in the art will recognize that the operation of the secondary latch 49 requires a separate motion by the caregiver that must be accomplished while the primary lever actuator is being manipulated. For example, the caregiver must depress the button 49*a* with his or her thumb while reaching outwardly with fingers to grasp the lever 46.

Figure 18:
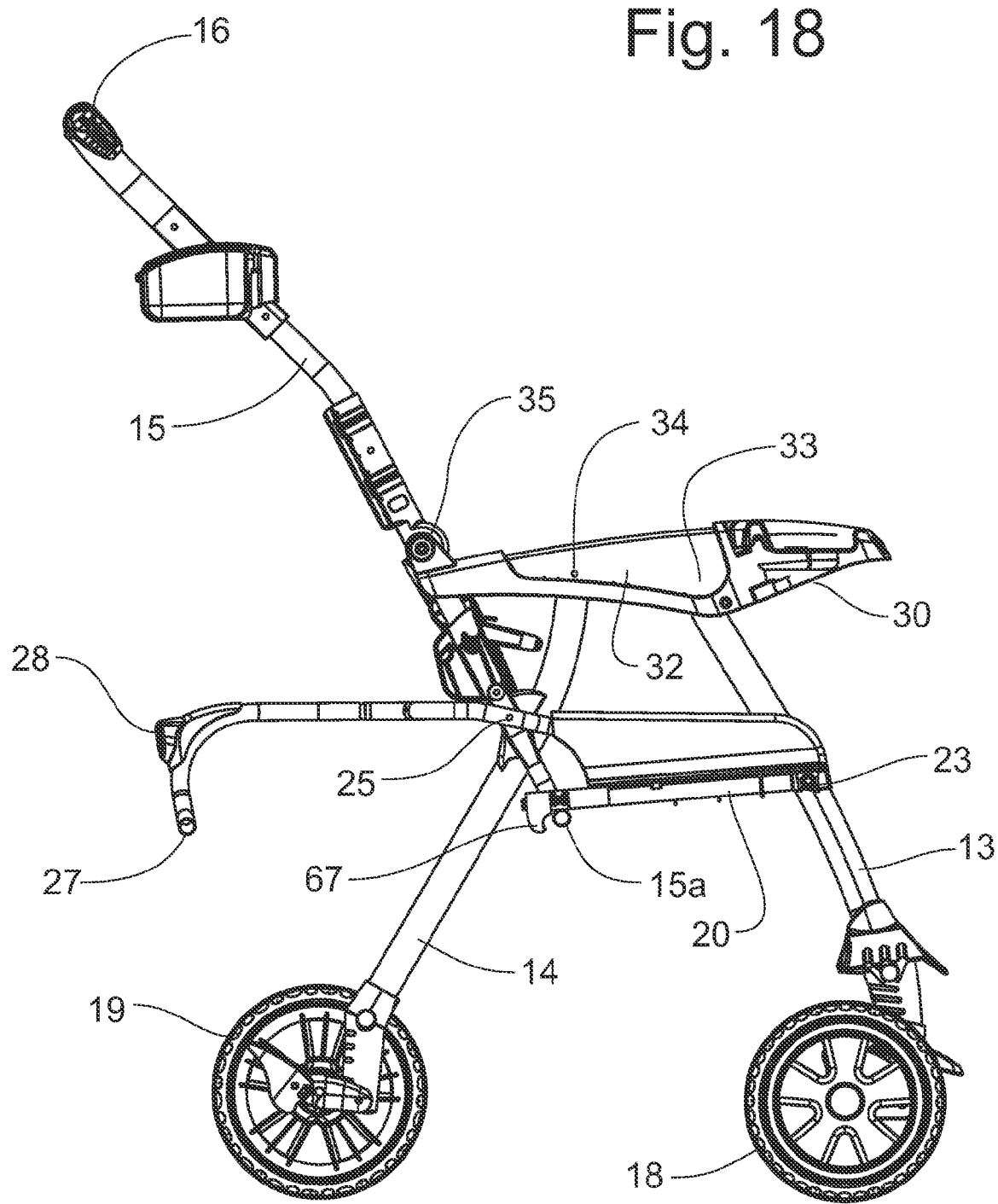
FIG. 18 is a schematic cross-sectional view through the center of the stroller frame placed in the operative position with the frame expanded and locked into place.
Figure 22:
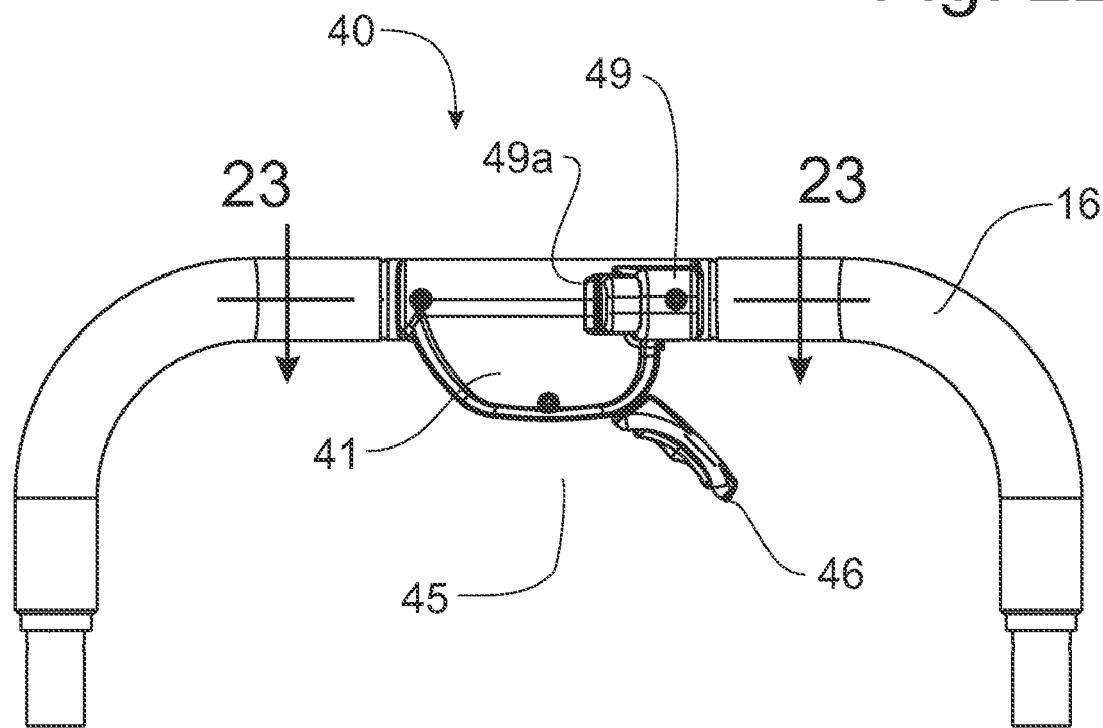
FIG. 22 is an enlarged bottom plan view of the handle of the stroller depicting the trigger fold mechanism actuator and the secondary latch button.
Figure 23:
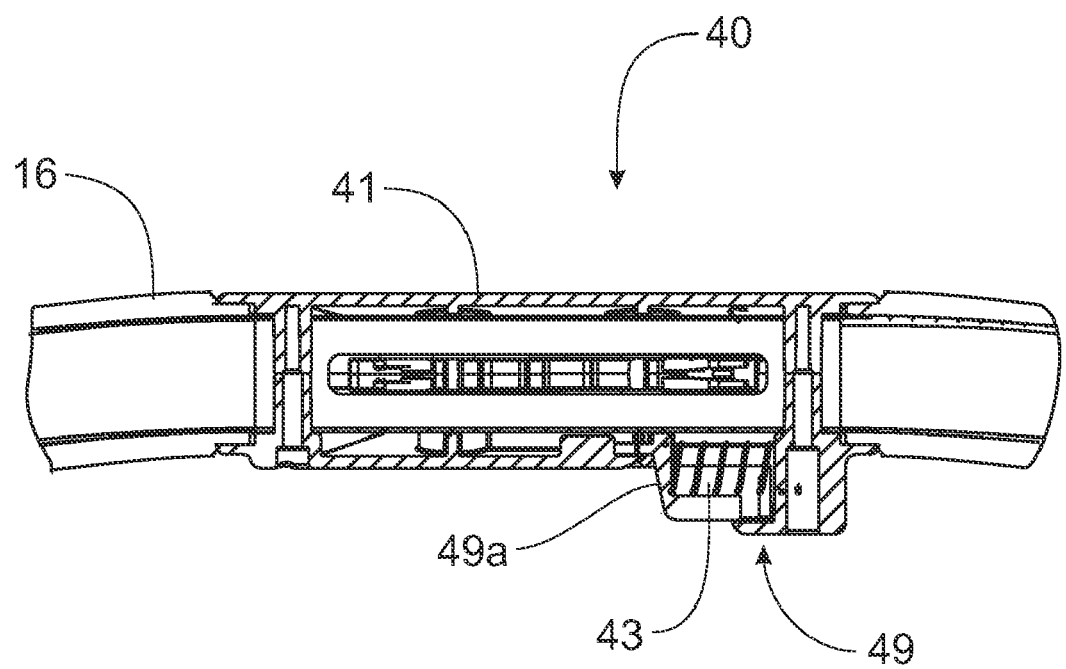
FIG. 23 is an enlarged partial cross-sectional view of the fold actuator mechanism taken along lines 23-23 of FIG. 22.

The operation of the spring assist mechanism 50 and the anti-fold latch mechanism 60 can best be seen in FIGS. 18-21A. In FIG. 18, the stroller frame 12 is oriented in the operative, expanded configuration, and a child is seated on the seat pan 22, which is determined by the seat pan 22 being lowered into engagement with the rear cross bar 15*a* and the compression of the spring 69. The hook members 67 are spaced rearwardly slightly of the rear cross bar 15*a* to insure that the anti-fold latch mechanism 60 clears the rear cross bar 15*a*, and provides a positive reinforcement through the feel of the rear cross bar 15*a* engaging the hook members 67, as is depicted in FIG. 19, if the latch mechanism 40 is actuated when the child is still seated on the seat pan 22.

Assuming the child has been appropriately removed from the stroller 10, the release of the latch mechanism 40 through manipulation of the latch actuation mechanism 45, including manipulation of the trigger lever 46 and the secondary latch 49, retracts the latch members 42 from the rear legs 14, thus allowing the articulation of the handle tubes 15 relative to the stabilizer members 17 about the articulation pivot 17*a*. Since the child is not present in the seat pan 22, the hook members 67 are located above the rear cross bar 15*a* permitting the rear cross bar 15*a* to move rearwardly, clearing the hook members 67. With respect to the first embodiment of the anti-fold latch mechanism 60 described above, the lack of a child in the seat pan allows the spring 63 to raise the trap member 62 and move the hook member 64 out of engagement with the gas spring mount and the rear cross bar 15*a*.

The spring assist mechanism 50, irrespective of which embodiment, will then be able to drive the folding movement of the stroller frame 12 into the compact storage configuration depicted in FIG. 21A. The stroller 10 can then be stood on the feet 28 appropriately located on the rearward end of the basket tube 27 and against the rear wheels 19 to position the folded stroller 10 in an upright orientation. Accordingly, the caregiver operating the stroller 10 need only move the latch actuation mechanism 45 and the stroller 10 automatically folds itself from the expanded operative configuration into the compact folded configuration without any extra effort to move the frame components. Conversely, the caregiver, when opening the stroller 10 from the storage position into the expanded operative position, will have to overcome the spring biasing forces urging the stroller frame 12 into the storage configuration. When the latch mechanism 40 is locked with the latch members 42 engaging the rear legs 14, the spring assist mechanism 50 is storing kinetic energy to be released with the latch members 42 disengaging the rear legs 14.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

Having thus described the invention, what is claimed is:

1. A stroller for transporting a child comprising:
    a frame having front legs and rear legs terminating in ground engaging wheels, and a handle assembly which are pivotally interconnected to permit said frame to be positionable between an expanded operative configuration and a collapsed storage configuration; and
    a spring assist mechanism supported on said frame and being operable to bias said frame for pivotal movement into said storage configuration; and
    an anti-fold latch including a pivotable trap member responsive to a positioning of said child on a seat assembly of said stroller to cause interference between said trap member and at least one selected component of said frame to prevent pivotal movement of said frame from said operative configuration into said storage configuration, said trap member being formed on a seat pan movable into interference with said at least one selected component of said frame, said seat pan being biased upwardly to urge said trap member away from interference with said at least one selected component of said frame.

2. The stroller of claim 1 wherein said frame includes a transverse front cross member extending between said front legs and a transverse rear cross member forming a part of said handle assembly, said trap member being pivoted for movement into interference with said rear cross member to prevent said rear cross member from moving away from said front cross member when a child is located on said seat assembly.

3. The stroller of claim 2 wherein the bias on said seat pan on which the child can be seated when said frame is in said operative configuration urges said trap member upwardly away from engagement with said rear cross member.

4. The stroller of claim 2 wherein said trap member includes a pair of hook members extending downwardly from said seat pan for engagement with said rear cross member, said seat pan being pivotally supported from said front legs and spring-loaded such that a child located on said seat pan causes pivotal movement of said seat pan to move said hook members into an interference position with respect to said rear cross member.

5. The stroller of claim 2 wherein said spring assist mechanism includes a spring member interconnecting two portions of said frame that are closer together when said frame is in said operative configuration than when said frame is in said storage configuration.

6. The stroller of claim 5 wherein said spring member is a gas spring.

7. The stroller of claim 6 wherein said frame includes a transverse front cross member extending between said front legs and a transverse rear cross member forming a part of said handle assembly, said gas spring being centrally positioned on said front and rear cross members.

8. The stroller of claim 2 wherein said spring assist mechanism includes a torsion spring interconnecting two pivotally connected components of said frame and arranged to bias pivotal movement of said frame components toward said collapsed storage configuration.

9. The stroller of claim 2 wherein said spring assist mechanism includes a pair of said torsion springs, one of said torsion springs being located on each side of said stroller in engagement with said handle assembly.

10. The stroller of claim 5 wherein said spring member includes a pair of compression springs mounted in corresponding telescopic tubular members located on opposing sides of said frame.

11. The stroller of claim 5 wherein said spring member includes a pair of laterally spaced elastomeric members that interconnect two frame components such that said elastomeric members are stretched to provide a spring force when said stroller is in said expanded operative position.

12. A stroller for transporting a child comprising:
a frame having front legs and rear legs terminating in ground engaging wheels, and an articulated handle assembly which are pivotally interconnected to permit said frame to be positionable between an expanded operative configuration and a collapsed storage configuration in conjunction with the articulation of said handle assembly;
a seat assembly pivotally connected to said frame, said seat assembly including a seat pan on which the child can be seated when said frame is in said operative configuration;
a latch mechanism operably supported on said handle assembly to secure said frame in said expanded operative configuration, said latch mechanism being selectively releasable to permit said frame to move into said storage configuration;
a spring assist mechanism supported on said frame and being operable to bias said frame for pivotal movement into said storage configuration when said latch mechanism is released; and
an anti-fold mechanism operatively supported from said frame to be engagable with said frame when a child is located on said seat pan to prevent said frame from moving into said collapsed storage configuration even when said latch mechanism is released, said anti-fold latch including a biased trap member engagable with said frame when a child is located on said seat pan to interfere with pivotal movement of said frame, said trap member being pivotally supported on said seat pan to be movable into engagement with said frame to prevent pivotal movement thereof, said trap member being biased into a raised position that does not engage said frame.

13. The stroller of claim 12 wherein said frame includes a front cross member extending between said front legs and a rear cross member extending between said handle tubes, said trap member having a pair of downwardly extending hook members to be engagable with said rear cross member to interfere with movement of said rear cross member relative to said front cross member when a child is located on said seat pan.

14. The stroller of claim 13 wherein said spring assist mechanism includes a gas spring interconnecting said front and rear cross members and being located beneath said trap member, said gas spring being connected to said rear cross member by a mounting bracket, said hook members being operable to engage said mounting bracket when depressed from said raised position when a child is located on said seat pan.

15. The stroller of claim 12 wherein said frame includes a front cross member extending between said front legs and a rear cross member extending between said handle tubes, said seat pan being pivotally mounted about a forward end thereof and spring-loaded into a raised position such that a rearward end of said seat pan is vertically movable about a generally horizontal pivot axis at said forward end, said trap member including a hook member extending downwardly from said rearward end of said seat pan to be engagable with said rear cross member when said seat pan is pivoted from said raised position in response to a child located on said seat pan.

16. The stroller of claim 15 wherein said spring member includes at least one torsion spring located on each side of said stroller at an articulation pivot in said handle assembly to bias articulation of said handle assembly to pivot said frame toward said collapsed storage configuration.

17. The stroller of claim 15 wherein said seat pan includes a torsion spring mounted at said horizontal pivot axis to bias said seat pan into said raised position.

18. The stroller of claim 15 wherein said seat pan includes a compression spring mounted at said rearward end to be engagable with said rear cross member to bias said seat pan into said raised position.

19. A stroller for transporting a child comprising:
a frame having front legs and rear legs terminating in ground engaging wheels, and an articulated handle assembly which are pivotally interconnected to permit said frame to be positionable between an expanded operative configuration and a collapsed storage configuration in conjunction with the articulation of said handle assembly;
a seat assembly pivotally connected to said frame, said seat assembly including a seat pan on which the child can be seated when said frame is in said operative configuration;
a latch mechanism operably supported on said handle assembly to secure said frame in said expanded operative configuration, said latch mechanism being selectively releasable to permit said frame to move into said storage configuration; and
an anti-fold mechanism operatively supported from said seat assembly to be engagable with a frame member when a child is located on said seat pan to prevent said frame from moving into said collapsed storage configuration even when said latch mechanism is released, said anti-fold mechanism including a hook member extending downwardly from said seat pan for engagement with said frame member, said seat pan being pivotally supported from said frame and being spring-loaded upwardly away from said frame member such that a child located on said seat pan causes pivotal movement of said seat pan to move said hook member into an interference position with respect to said frame member.

20. The stroller of claim 19 wherein said frame includes a transverse rear cross member forming a part of said handle assembly, said anti-fold mechanism including a pair of hook members extending downwardly from said seat pan for engagement with said rear cross member, said seat pan being pivotally supported from said front legs and spring-loaded such that a child located on said seat pan causes pivotal movement of said seat pan to move said hook members into an interference position with respect to said rear cross member.

21. The stroller of claim 20 further comprising a spring assist mechanism supported on said frame and being operable to bias said frame for pivotal movement into said storage configuration when said latch mechanism is released.

22. The stroller of claim 19, wherein said handle assembly includes a pair of handle tubes connected at an upper portion thereof to form a handle bar, said front legs, rear legs and handle assembly being pivotally interconnected to permit said frame to be positionable between an expanded operative configuration and a collapsed storage configuration, and said latch mechanism comprises:
   a housing operably supported on said handle assembly;
   a pair of latch members operably mounted to secure said frame in said expanded operative configuration; and
   a latch actuation mechanism mounted on the handle bar and being coupled with the latch members to affect movement thereof between a latched position and an unlatched position, said latch actuation mechanism including a pair of interengaged gears rotatably mounted in said housing for rotation about corresponding laterally spaced axes of rotation, said latch actuation mechanism including a lever connected directly to one of said gears and extending radially with respect to said one of said gears to project outwardly of said housing to allow engagement thereof to affect rotational movement of said one of said gears and the other of said gears through the engagement thereof with said one of said gears, thereby causing a corresponding movement of said latch members.

23. The stroller of claim 22 wherein manipulation of said one of said gears having said lever extending therefrom affects rotation of said one gear and, due to the interengagement of the gears, the rotation of the other said gear, each said gear being connected to the corresponding said latch member such that the rotation of each said gear causes a movement of the corresponding said latch member.

24. The stroller of claim 23 further comprising a secondary latch mounted on said housing and being cooperable with said latch actuation mechanism to prevent movement of said latch members unless said secondary latch is previously actuated.

25. The stroller of claim 24 wherein said secondary latch is movable between a locked position in which said latch actuation mechanism cannot be operated and an unlocked position in which said latch actuation mechanism is free to move, at least one of said gears being formed with an abutment engagable with said secondary latch when in said locked position.

26. The stroller of claim 25 wherein said secondary latch is formed as a spring-loaded button mounted in said housing, said button having a protrusion positionable in an interfering engagement with said abutment on said one gear, said button being depressible into said housing to displace said protrusion from interference with said abutment.

27. The stroller of claim 26 further comprising:
   a spring assist mechanism supported on said frame and being operable to bias said frame for pivotal movement into said storage configuration when said latch mechanism moves said latch members into said unlatched position.

28. The stroller of claim 27 further comprising:
   a seat assembly supported from said frame on which a child can be seated when said frame is in said operative configuration; and
   an anti-fold latch operatively associated with said seat assembly to prevent pivotal movement of said frame from said operative configuration into said storage configuration when the child is located on said seat assembly.

* * * * *